US012595519B2

(12) United States Patent
Howell et al.

(10) Patent No.: US 12,595,519 B2
(45) Date of Patent: Apr. 7, 2026

(54) **MOLECULAR MARKERS FOR REDUCED PYRUVATE LEVEL TRAIT IN *ALLIUM CEPA***

(71) Applicant: Nunhems B.V., Nunhem (NL)

(72) Inventors: Tyson Ronald Howell, Brooks, OR (US); Juan Carlos Brevis Acuna, Brooks, OR (US); Ebenezer A. Ogundiwin, Davis, CA (US); Cathy M. Pham-Nguyen, West Sacramento, CA (US); Elly Soeryapranata, Davis, CA (US)

(73) Assignee: NUNHEMS B.V., Nunhem (NL)

( * ) Notice: Subject to any disclaimer, the term of this patent is extended or adjusted under 35 U.S.C. 154(b) by 393 days.

(21) Appl. No.: 17/779,981

(22) PCT Filed: Nov. 26, 2020

(86) PCT No.: PCT/EP2020/083533
§ 371 (c)(1),
(2) Date: May 25, 2022

(87) PCT Pub. No.: WO2021/105296
PCT Pub. Date: Jun. 3, 2021

(65) Prior Publication Data
US 2023/0340620 A1 Oct. 26, 2023

Related U.S. Application Data

(60) Provisional application No. 62/940,667, filed on Nov. 26, 2019.

(30) Foreign Application Priority Data

Dec. 16, 2019 (EP) ..................................... 19216666
Apr. 20, 2020 (EP) ..................................... 20170450

(51) Int. Cl.
*C12Q 1/6895* (2018.01)
*A01H 1/04* (2006.01)
*A01H 6/04* (2018.01)

(52) U.S. Cl.
CPC ........... *C12Q 1/6895* (2013.01); *A01H 1/045* (2021.01); *A01H 6/045* (2018.05); *C12Q 2600/13* (2013.01); *C12Q 2600/156* (2013.01)

(58) Field of Classification Search
None
See application file for complete search history.

(56) References Cited

U.S. PATENT DOCUMENTS 8,816,155 B2 * 8/2014 Watson ................... A01H 6/045
800/298
2007/0016984 A1 1/2007 Hendricks
2020/0288658 A1 * 9/2020 Watson .................... A01H 5/06

FOREIGN PATENT DOCUMENTS

EP 0534858 A1 3/1993
EP 2992756 A1 3/2016
WO 2007/011857 A2 1/2007
WO 2009/092560 A1 7/2009

OTHER PUBLICATIONS

McCallum et al., Theoretical and Applied Genetics 114 (2007): 815-822 (Year: 2007).*
Khosa, Jiffinvir S., et al. "Enhancing onion breeding using molecular tools." Plant Breeding 135.1 (2016): 9-20. (Year: 2016).*
Jones, Henry Albert, and Samuel Leonard Emsweller. "Methods of breeding onions." (1933): 625-42. (Year: 1933).*
Collard, Bertrand CY, et al. "An introduction to markers, quantitative trait loci (QTL) mapping and marker-assisted selection for crop improvement: the basic concepts." Euphytica 142 (2005): 169-196. (Year: 2005).*
GenBank Accession No. AF165818.4 "Guillardia theta nucleomorph chromosome 1, complete sequence" dated Jul. 20, 2016 https://www.ncbi.nlm.nih.gov/nuccore/AF165818.4 (Year: 2016).*
Galmarini, Claudio R. Quantitative trait loci controlling solids, pungency, and antiplatelet activity in onion (*Allium cepa* L.). Diss. The University of Wisconsin-Madison, 2000. (Year: 2000).*
"601650507R1 NIH_MGC_76 *Homo sapiens* cDNA clone Image:3934272 3', mRNA sequence", Database EMBL [Online], retrieved from EBI Database accession No. BF126718, XP055701414, Oct. 26, 2000, 1 page.
"Mytilus galloprovincialis breed Wild contig_533286, whole genome shotgun sequence.", Database EMBL [Online], retrieved from EBI Database accession No. LNJA010533210, XP055701473, Dec. 7, 2018, 1 page.
"Nicotiana tabacum cDNA, clone: TBK02GR0055_1_G01, 5'-end sequence.", Database EMBL [Online], retrieved from EBI Database accession No. FS420664, XP055701479, Jul. 24, 2009, 1 page.

(Continued)

*Primary Examiner* — Amjad Abraham
*Assistant Examiner* — Kelsey L McWilliams
(74) *Attorney, Agent, or Firm* — ArentFox Schiff LLP

(57) ABSTRACT

The present invention relates to a genetic marker for determining the presence or absence of one or more QTLs conferring a reduced pyruvate level in an *Allium cepa* plant or plant part, wherein the marker is selected from the group consisting of a marker linked to a reduced pyruvate conferring QTL located on chromosome 2, a marker linked to a reduced pyruvate conferring QTL located on chromosome 1 and a marker linked to a reduced pyruvate conferring QTL located on chromosome 7. The present invention further relates to the use of the marker of the invention for determining the presence or absence of one or more QTLs conferring a reduced pyruvate level in an *Allium cepa* plant or plant part. The present invention further relates to a method for identifying and/or selecting an *Allium cepa* plant or plant part comprising determining in the plant or plant part the presence or absence of one or more markers of the invention. The present invention relates to isolated nucleic acid and the use of the nucleotide sequences as provided herein for marker assisted selection of an *Allium cepa* plant or plant part.

7 Claims, No Drawings

Specification includes a Sequence Listing.

(56)                    References Cited

OTHER PUBLICATIONS

"Roth2-MLV3p-CD4T-20100730Well1NIalll-GQKH UJB02BWRMZ Gammaretroviral integration into nucleosomal target DNA library *Homo sapiens* genomic, genomic surve sequence", Database EMBL [Online], retrieved from EBI accession No. JJ873402, XP055934455, May 3, 2011.

"Sequence 300809 from U.S. Pat. No. 7,618,814", Database EMBL [Online], retrieved from EBI accession No. GV300809, XP055805231, Dec. 25, 2009, 1 page.

"Sequence 328311 from Patent WO2005116250", Database EMBL [Online], retrieved from EBI accession No. GM377633, XP055805262, Jan. 23, 2009, 1 page.

"Sequence 79358 from U.S. Pat. No. 736,146", Database EMBL [Online], retrieved from EBI accession No. EA580733, XP055805259, Jun. 12, 2008, 1 page.

"Sphingomyelin synthase 1 (SGMSI) gene-trap integration site DNA SEQ:38", Database Geneseq [Online], retrieved from EBI accession No. AYN68858, XP055805238, Mar. 3, 2011, 1 page.

Allen, et al., "Transcript-specific, single-nucleotide polymorphism discovery and linkage analysis in hexaploid bread wheat (*Triticum aestivum* L.)", Plant Biotechnology Journal, vol. 9, Issue 9, Jun. 1, 2011, pp. 1086-1099.

Anthon, et al., "Modified method for the determination of pyruvic acid with dinitrophenylhydrazine in the assessment of onion pungency", Journal of the Science of Food and Agriculture, vol. 83, Issue 12, Aug. 5, 2003, pp. 1210-1213.

Duangjit, et al., "Transcriptome sequencing to produce SNP-based genetic maps of onion", Theoretical and Applied Genetics, vol. 126, Issue 8, May 21, 2013, pp. 2093-2101.

European Search Report for EP Patent Application No. 19216666.8, Issued on Sep. 17, 2020, 6 pages.

Foskett, et al., "Relation of dry matter content to storage quality in some onion varieties and hybrids", Proceedings of the American Society for Horticultural Science, vol. 55, 1950, pp. 314-318.

Havey, et al., "Informativeness of Single Nucleotide Polymorphisms and Relationships among Onion Populations from Important World Production Regions", Journal of the American Society for Horticultural Science, vol. 143, Issue 1, Jan. 2018, pp. 34-44.

Henikoff, et al., "Amino acid substitution matrices from protein blocks", Proceedings of the National Academy of Sciences, vol. 89, Issue 22, Nov. 15, 1992, pp. 10915-10919.

International Search Report for PCT Patent Application No. PCT/EP2020/083533, Issued on Jun. 23, 2021, 6 pages.

Jo, et al., "Development of a Genetic Map for Onion (*Allium cepa* L.) Using Reference-Free Genotyping-by-Sequencing and SNP Assays", Frontiers in Plant Science, vol. 8, Article No. 1606, Sep. 14, 2017, 8 pages.

Lin, et al., "Inheritance of Soluble Solids and Pyruvic Acid Content of Bulb Onions", Journal of the American Society for Horticultural Science, vol. 120, Issue 1, Jan. 1995, pp. 119-122.

Mann, et al., "Use of the refractometer for selecting onion bulbs high in dry matter for breeding", Proceedings of the American Society for Horticultural Science, vol. 46, 1945, pp. 285-292.

McCallum, et al., "Genetic mapping of sulfur assimilation genes reveals a QTL for onion bulb pungency", Theoretical and Applied Genetics, vol. 114, Dec. 16, 2006, pp. 815-822.

Michael J. Havey, "Genetic Mapping of Chartreuse Bulb Color in Onion", Journal of the American Society for Horticultural Science, vol. 145, Issue 2, Mar. 2020, pp. 110-119.

Munaiz, et al., "Genetic Analyses of Epicuticular Waxes Associated with the Glossy Foliage of 'White Persian' Onion", Journal of the American Society for Horticultural Science, vol. 145, Issue 1, Jan. 2020, pp. 67-72.

Philipp W. Simon, "Genetic analysis of pungency and soluble solids in long-storage onions", Euphytica, vol. 82, Issue 1, Jan. 1995, pp. 1-8.

Randle, et al., "Pungency and Sugars of Short-day Onions as Affected by Sulfur Nutrition", Journal of the American Society for Horticultural Science, vol. 118, Issue 6, Nov. 1993, pp. 766-770.

Schwimmer, et al., "Onion Flavor and Odor, Enzymatic Development of Pyruvic Acid in Onion as a Measure of Pungency", Journal of Agricultural and Food Chemistry, vol. 9, Issue 4, Jul. 1, 1961, pp. 301-304.

Schwimmer, et al., "Relation Between Olfactory Threshold Concentration and Pyruvic Acid Content of Onion Juice", Journal of Food Science, vol. 27, Issue 1, Jan. 1962, pp. 94-97.

Shock, et al., "Effect Of Onion Bulb Temperature And Handling On Bruising", Malheur Experiment Station, Oregon State University, 2005, 5 pages.

Tsukazaki, et al., "Development of transcriptome shotgun assembly-derived markers in bunching onion (*Allium fistulosum*)", Molecular Breeding, vol. 35, Jan. 25, 2015, pp. 1-11.

Tsukazaki, et al., "QTL analysis for pseudostem pungency in bunching onion (*Allium fistulosum*)", Molecular Breeding, vol. 30, Issue 4, Jun. 12, 2012, pp. 1689-1698.

Wall, et al., "Heritability estimates and progeny testing of phenotypic selections for soluble solids content in dehydrator onion", Euphytica, vol. 106, Issue 1, Mar. 1999, pp. 7-13.

Wall, et al., "Heritability estimates and response to selection for the pungency and single center traits in onion", Euphytica, vol. 87, Issue 2, Jan. 1996, pp. 133-139.

Wall, et al., "Relationship between Pyruvate Analysis and Flavor Perception for Onion Pungency Determination", HortScience, vol. 27, Issue 9, Sep. 1992, pp. 1029-1030.

William M. Randle, "Onion germplasm interacts with sulfur fertility for plant sulfur utilization and bulb pungency", Euphytica, vol. 59, Issue 2, Feb. 1992, pp. 151-156.

* cited by examiner

SEQUENCE LISTING

<160> NUMBER OF SEQ ID NOS: 62

<210> SEQ ID NO 1
<211> LENGTH: 101
<212> TYPE: DNA
<213> ORGANISM: Allium cepa

<400> SEQUENCE: 1

-continued

```
catggcaaga aaaatgttcc aagcttcttg aaacatctcc agacaattgg tctttcaaaa      60
gtgattccga aacctctact tcgaagtaca ttgcttcttt a                          101

<210> SEQ ID NO 2
<211> LENGTH: 101
<212> TYPE: DNA
<213> ORGANISM: Allium cepa

<400> SEQUENCE: 2
catggcaaga aaaatgttcc aagcttcttg aaacatctcc agacaattgg gctttcaaaa      60
gtgattccga aacctctact tcgaagtaca ttgcttcttt a                          101

<210> SEQ ID NO 3
<211> LENGTH: 101
<212> TYPE: DNA
<213> ORGANISM: Allium cepa

<400> SEQUENCE: 3
ttgataaaag cgatattgtt ggggaagtat cctgcagaat ttttgtggcc atgaaaagga      60
agatgagtgg aagctaaatg cattggaaat tgtgtttggc c                          101

<210> SEQ ID NO 4
<211> LENGTH: 101
<212> TYPE: DNA
<213> ORGANISM: Allium cepa

<400> SEQUENCE: 4
ttgataaaag cgatattgtt ggggaagtat cctgcagaat ttttgtggcc gtgaaaagga      60
agatgagtgg aagctaaatg cattggaaat tgtgtttggc c                          101

<210> SEQ ID NO 5
<211> LENGTH: 101
<212> TYPE: DNA
<213> ORGANISM: Allium cepa

<400> SEQUENCE: 5
gacggataat tcagaacagg gaggaagtaa gcagcatgtg ataatcaaca cagaggatag      60
agcttctgag gtgggtaaag ctgatgcgaa tcgtcccacg c                          101

<210> SEQ ID NO 6
<211> LENGTH: 101
<212> TYPE: DNA
<213> ORGANISM: Allium cepa

<400> SEQUENCE: 6
gacggataat tcagaacagg gaggaagtaa gcagcatgtg ataatcaaca tagaggatag      60
agcttctgag gtgggtaaag ctgatgcgaa tcgtcccacg c                          101

<210> SEQ ID NO 7
<211> LENGTH: 101
<212> TYPE: DNA
<213> ORGANISM: Allium cepa

<400> SEQUENCE: 7
tgatgctatc tggaagatta caaatttata gatggtatgg gatgttggaa tagcagattg      60
gtgctgaatt tagtactacc aaaggacaga tgacgccgct t                          101

<210> SEQ ID NO 8
```

-continued

```
<211> LENGTH: 101
<212> TYPE: DNA
<213> ORGANISM: Allium cepa

<400> SEQUENCE: 8
tgatgctatc tggaagatta caaatttata gatggtatgg gatgttggaa cagcagattg      60
gtgctgaatt tagtactacc aaaggacaga tgacgccgct t                         101

<210> SEQ ID NO 9
<211> LENGTH: 101
<212> TYPE: DNA
<213> ORGANISM: Allium cepa

<400> SEQUENCE: 9
ctcaggaatg agatttgcat cagcatcctc aggatcaatt tcttgatcat cagattgcat      60
tccataatta aacagcagct cgtgccactt catgtcatca a                         101

<210> SEQ ID NO 10
<211> LENGTH: 101
<212> TYPE: DNA
<213> ORGANISM: Allium cepa

<400> SEQUENCE: 10
ctcaggaatg agatttgcat cagcatcctc aggatcaatt tcttgatcat tagattgcat      60
tccataatta aacagcagct cgtgccactt catgtcatca a                         101

<210> SEQ ID NO 11
<211> LENGTH: 101
<212> TYPE: DNA
<213> ORGANISM: Allium cepa

<400> SEQUENCE: 11
cctgagcgat gtaaaaggaa gagatagagt atgggagttg agaaactgta accatgtttt      60
tcataaagga tgcctggaca aatggttaga gcatgatgag c                         101

<210> SEQ ID NO 12
<211> LENGTH: 101
<212> TYPE: DNA
<213> ORGANISM: Allium cepa

<400> SEQUENCE: 12
cctgagcgat gtaaaaggaa gagatagagt atgggagttg agaaactgta gccatgtttt      60
tcataaagga tgcctggaca aatggttaga gcatgatgag c                         101

<210> SEQ ID NO 13
<211> LENGTH: 101
<212> TYPE: DNA
<213> ORGANISM: Allium cepa

<400> SEQUENCE: 13
gattgtttag acattcgttg tatttcgcga gatctgctca cgggatagct catttttaa       60 gatttttcga gaaattctac ctggattttt gttagggttt t                         101

<210> SEQ ID NO 14
<211> LENGTH: 101
<212> TYPE: DNA
<213> ORGANISM: Allium cepa

<400> SEQUENCE: 14
gattgtttag acattcgttg tatttcgcga gatctgctca cgggatagct gatttttaa       60
```

-continued

```
gatttttcga gaaattctac ctggattttt gttagggttt t                        101

<210> SEQ ID NO 15
<211> LENGTH: 101
<212> TYPE: DNA
<213> ORGANISM: Allium cepa

<400> SEQUENCE: 15
aattacactt tagcaatcaa gagatgattc tcaggagaaa tatccgagga tgtatacttc    60
accatttgtg catccaaccc ctgatccctt agccacgaca t                        101

<210> SEQ ID NO 16
<211> LENGTH: 101
<212> TYPE: DNA
<213> ORGANISM: Allium cepa

<400> SEQUENCE: 16
aattacactt tagcaatcaa gagatgattc tcaggagaaa tatccgagga ggtatacttc    60
accatttgtg catccaaccc ctgatccctt agccacgaca t                        101

<210> SEQ ID NO 17
<211> LENGTH: 101
<212> TYPE: DNA
<213> ORGANISM: Allium cepa

<400> SEQUENCE: 17
gatgatggtg gagcgagaag agaatggttc tggtttgtgg tttgattgga tgggtttgtc    60
gatcgaggtc catgaccatt gcttgtggat gcggttccat c                        101

<210> SEQ ID NO 18
<211> LENGTH: 101
<212> TYPE: DNA
<213> ORGANISM: Allium cepa

<400> SEQUENCE: 18
gatgatggtg gagcgagaag agaatggttc tggtttgtgg tttgattgga cgggtttgtc    60
gatcgaggtc catgaccatt gcttgtggat gcggttccat c                        101

<210> SEQ ID NO 19
<211> LENGTH: 101
<212> TYPE: DNA
<213> ORGANISM: Allium cepa

<400> SEQUENCE: 19
gagcaagatc agttaagatt cttaaagctc tttgaagaca ccgatgagtt ggatgatgag    60
ttggaacaat tataagttca atctactacg ccatacttta c                        101

<210> SEQ ID NO 20
<211> LENGTH: 101
<212> TYPE: DNA
<213> ORGANISM: Allium cepa

<400> SEQUENCE: 20
gagcaagatc agttaagatt cttaaagctc tttgaagaca ccgatgagtt cgatgatgag    60
ttggaacaat tataagttca atctactacg ccatacttta c                        101

<210> SEQ ID NO 21
<211> LENGTH: 101
<212> TYPE: DNA
```

-continued

```
<213> ORGANISM: Allium cepa

<400> SEQUENCE: 21
acttatttgt accagatgct agttcatcat acgatctcga tcaacagctc aaaactgtcc        60
ccacttcatc tgacggcaat atcatggttt cttggaatcc t                          101

<210> SEQ ID NO 22
<211> LENGTH: 101
<212> TYPE: DNA
<213> ORGANISM: Allium cepa

<400> SEQUENCE: 22
acttatttgt accagatgct agttcatcat acgatctcga tcaacagctc gaaactgtcc        60
ccacttcatc tgacggcaat atcatggttt cttggaatcc t                          101

<210> SEQ ID NO 23
<211> LENGTH: 101
<212> TYPE: DNA
<213> ORGANISM: Allium cepa

<400> SEQUENCE: 23
actcttttca aaatggcaat ccaaaactt gaactttaac ttttgttaca cgcttaatca        60
cgtcgataat catgcttagc accactgcca ctttctaaat c                          101

<210> SEQ ID NO 24
<211> LENGTH: 101
<212> TYPE: DNA
<213> ORGANISM: Allium cepa

<400> SEQUENCE: 24
actcttttca aaatggcaat ccaaaactt gaactttaac ttttgttaca tgcttaatca        60
cgtcgataat catgcttagc accactgcca ctttctaaat c                          101

<210> SEQ ID NO 25
<211> LENGTH: 101
<212> TYPE: DNA
<213> ORGANISM: Allium cepa

<400> SEQUENCE: 25
cctgaacatt atgcaaaatg tttagccaca ctttcacgct catcttcact tggaattcga        60
ttgtgttttc gtcagtacag taaaaataaa ttcaagcttt t                          101

<210> SEQ ID NO 26
<211> LENGTH: 101
<212> TYPE: DNA
<213> ORGANISM: Allium cepa

<400> SEQUENCE: 26
cctgaacatt atgcaaaatg tttagccaca ctttcacgct catcttcact aggaattcga        60
ttgtgttttc gtcagtacag taaaaataaa ttcaagcttt t                          101

<210> SEQ ID NO 27
<211> LENGTH: 101
<212> TYPE: DNA
<213> ORGANISM: Allium cepa

<400> SEQUENCE: 27
cgtgaaagtg tggctaaaca ttttgcataa tgttcaggag ttaaaaccac agcaatgtca        60
tctatacatt ctgcgctgat cacttgtgag aagggcgtga a                          101
```

-continued

```
<210> SEQ ID NO 28
<211> LENGTH: 101
<212> TYPE: DNA
<213> ORGANISM: Allium cepa

<400> SEQUENCE: 28
cgtgaaagtg tggctaaaca ttttgcataa tgttcaggag ttaaaaccac ggcaatgtca      60
tctatacatt ctgcgctgat cacttgtgag aagggcgtga a                         101

<210> SEQ ID NO 29
<211> LENGTH: 101
<212> TYPE: DNA
<213> ORGANISM: Allium cepa

<400> SEQUENCE: 29
taagcttcat gaagctatat atatcacagt aaaacaggtt attttttatgg gcatggatta     60 ctttttaaat ttgtaagttg gttttgtctc ccttttggtt a                         101

<210> SEQ ID NO 30
<211> LENGTH: 101
<212> TYPE: DNA
<213> ORGANISM: Allium cepa

<400> SEQUENCE: 30
taagcttcat gaagctatat atatcacagt aaaacaggtt attttttatgg acatggatta     60 ctttttaaat ttgtaagttg gttttgtctc ccttttggtt a                         101

<210> SEQ ID NO 31
<211> LENGTH: 101
<212> TYPE: DNA
<213> ORGANISM: Allium cepa

<400> SEQUENCE: 31
acgtcggcgg gagctttctc ggtttgatac acgcctaaat agccggttgg atcgactctc      60
gcgtagatcg gaccgttgcc ttggattatt tgagttttgg c                         101

<210> SEQ ID NO 32
<211> LENGTH: 101
<212> TYPE: DNA
<213> ORGANISM: Allium cepa

<400> SEQUENCE: 32
acgtcggcgg gagctttctc ggtttgatac acgcctaaat agccggttgg gtcgactctc      60
gcgtagatcg gaccgttgcc ttggattatt tgagttttgg c                         101

<210> SEQ ID NO 33
<211> LENGTH: 101
<212> TYPE: DNA
<213> ORGANISM: Allium cepa

<400> SEQUENCE: 33
tatagtgtgg caaaaggtgc attgcataga gcatttgatg agatagtagt agttgaaaga      60
aattgtggtc gagaagagca gagagatcca atcaatatta a                         101

<210> SEQ ID NO 34
<211> LENGTH: 101
<212> TYPE: DNA
<213> ORGANISM: Allium cepa
```

-continued

```
<400> SEQUENCE: 34
tatagtgtgg caaaaggtgc attgcataga gcatttgatg agatagtagt tgttgaaaga      60
aattgtggtc gagaagagca gagagatcca atcaatatta a                         101

<210> SEQ ID NO 35
<211> LENGTH: 101
<212> TYPE: DNA
<213> ORGANISM: Allium cepa

<400> SEQUENCE: 35
tattataatt ataagcagtg atgtcacatt cattaatttg tgcaccctca ttattatccc      60
tcgatgaaaa gtcaattatt cgttaggaa tatccgtaga c                          101

<210> SEQ ID NO 36
<211> LENGTH: 101
<212> TYPE: DNA
<213> ORGANISM: Allium cepa

<400> SEQUENCE: 36
tattataatt ataagcagtg atgtcacatt cattaatttg tgcaccctca atattatccc      60
tcgatgaaaa gtcaattatt cgttaggaa tatccgtaga c                          101

<210> SEQ ID NO 37
<211> LENGTH: 101
<212> TYPE: DNA
<213> ORGANISM: Allium cepa

<400> SEQUENCE: 37
tgttgcattc cccattaccc aatatcactg tcacaactat gctccccaac tccttgctac      60
actgcaataa catcacatac aacttcactt ccccgaacaa c                         101

<210> SEQ ID NO 38
<211> LENGTH: 101
<212> TYPE: DNA
<213> ORGANISM: Allium cepa

<400> SEQUENCE: 38
tgttgcattc cccattaccc aatatcactg tcacaactat gctccccaac accttgctac      60
actgcaataa catcacatac aacttcactt ccccgaacaa c                         101

<210> SEQ ID NO 39
<211> LENGTH: 101
<212> TYPE: DNA
<213> ORGANISM: Allium cepa

<400> SEQUENCE: 39
cttcccctcg gtaaatattc tgttactatc gacaaatgtg gagactttgt gactgcaccc      60
ataaatagta caatatttgg atggcgaata cgtttcatta t                         101

<210> SEQ ID NO 40
<211> LENGTH: 101
<212> TYPE: DNA
<213> ORGANISM: Allium cepa

<400> SEQUENCE: 40
cttcccctcg gtaaatattc tgttactatc gacaaatgtg gagactttgt aactgcaccc      60
ataaatagta caatatttgg atggcgaata cgtttcatta t                         101
```

```
<210> SEQ ID NO 41
<211> LENGTH: 101
<212> TYPE: DNA
<213> ORGANISM: Allium cepa

<400> SEQUENCE: 41
tactgcccag tcactgcttg tggggatgga ttcttcgtct tcaagcgatg ctcgaattct        60
ctcaagatct ttctctgaag cttctttgaa attaatgtcc t                          101

<210> SEQ ID NO 42
<211> LENGTH: 101
<212> TYPE: DNA
<213> ORGANISM: Allium cepa

<400> SEQUENCE: 42
tactgcccag tcactgcttg tggggatgga ttcttcgtct tcaagcgatg ttcgaattct        60
ctcaagatct ttctctgaag cttctttgaa attaatgtcc t                          101

<210> SEQ ID NO 43
<211> LENGTH: 101
<212> TYPE: DNA
<213> ORGANISM: Allium cepa

<400> SEQUENCE: 43
gatacccaaa accctgatat gatcgactat ctcaaccaag aaaatgatta tactgaatca        60
tttatgaaag atactgaaaa attgcagcga aaattagtgg a                          101

<210> SEQ ID NO 44
<211> LENGTH: 101
<212> TYPE: DNA
<213> ORGANISM: Allium cepa

<400> SEQUENCE: 44
gatacccaaa accctgatat gatcgactat ctcaaccaag aaaatgatta cactgaatca        60
tttatgaaag atactgaaaa attgcagcga aaattagtgg a                          101

<210> SEQ ID NO 45
<211> LENGTH: 101
<212> TYPE: DNA
<213> ORGANISM: Allium cepa

<400> SEQUENCE: 45
ttatggtcga aagaagacct attgaacttt gtcatagcac ctccagtggg tatcttccca        60
cacagcttat tatagccgac gtcaaaatac accagtttga t                          101

<210> SEQ ID NO 46
<211> LENGTH: 101
<212> TYPE: DNA
<213> ORGANISM: Allium cepa

<400> SEQUENCE: 46
ttatggtcga aagaagacct attgaacttt gtcatagcac ctccagtggg catcttccca        60
cacagcttat tatagccgac gtcaaaatac accagtttga t                          101

<210> SEQ ID NO 47
<211> LENGTH: 101
<212> TYPE: DNA
<213> ORGANISM: Allium cepa

<400> SEQUENCE: 47
```

-continued

```
aaattggcta tggagaagat gaagattgat ttggcacaga aagataagat cctgtctgca        60
ttgctgagaa aatcaaaggc tgataatgaa gaaaagcata t                          101

<210> SEQ ID NO 48
<211> LENGTH: 101
<212> TYPE: DNA
<213> ORGANISM: Allium cepa

<400> SEQUENCE: 48
aaattggcta tggagaagat gaagattgat ttggcacaga aagataagat cctgtctgca        60
ttgctgagaa aatcaaaggc tgataatgaa gaaaagcata t                          101

<210> SEQ ID NO 49
<211> LENGTH: 101
<212> TYPE: DNA
<213> ORGANISM: Allium cepa

<400> SEQUENCE: 49
cattctgtca tggttatcag tcacatctaa tgatgcttta atactttccg gattcagaaa        60
tgacaaatgt gctccaccaa atgcttctac acatggttta c                          101

<210> SEQ ID NO 50
<211> LENGTH: 101
<212> TYPE: DNA
<213> ORGANISM: Allium cepa

<400> SEQUENCE: 50
cattctgtca tggttatcag tcacatctaa tgatgcttta atactttccg aattcagaaa        60
tgacaaatgt gctccaccaa atgcttctac acatggttta c                          101

<210> SEQ ID NO 51
<211> LENGTH: 121
<212> TYPE: DNA
<213> ORGANISM: Allium cepa

<400> SEQUENCE: 51
ctcgcttttg tctccggtca aatacttgaa cccatcatac aaaattcttt caaaaacgtc        60 cactttttatt tttccaacca acacccttttc agtactcttc tccaaaacag ataggaacaa       120
c                                                                      121

<210> SEQ ID NO 52
<211> LENGTH: 121
<212> TYPE: DNA
<213> ORGANISM: Allium cepa

<400> SEQUENCE: 52 ctcgctttttg tctccggtca aatacttgaa cccatcatac aaaattcttt caaaaacgtc       60 aactttttatt tttccaacca acacccttttc agtactcttc tccaaaacag ataggaacaa      120
c                                                                      121

<210> SEQ ID NO 53
<211> LENGTH: 121
<212> TYPE: DNA
<213> ORGANISM: Allium cepa
<220> FEATURE:
<221> NAME/KEY: misc_feature
<222> LOCATION: (1)..(1)
<223> OTHER INFORMATION: n is a, c, g, or t

<400> SEQUENCE: 53
```

-continued

```
naatcgagcg gagttcgtcg gagtccatta ccgtctcttt ctttggctat ttaatatcgt      60
gtaatggagg ataaaagagg ataatgatgt aatattttat ggattggact atataaaaat     120
g                                                                      121

<210> SEQ ID NO 54
<211> LENGTH: 121
<212> TYPE: DNA
<213> ORGANISM: Allium cepa
<220> FEATURE:
<221> NAME/KEY: misc_feature
<222> LOCATION: (1)..(1)
<223> OTHER INFORMATION: n is a, c, g, or t

<400> SEQUENCE: 54
naatcgagcg gagttcgtcg gagtccatta ccgtctcttt ctttggctat ttaatatcgt      60
ttaatggagg ataaaagagg ataatgatgt aatattttat ggattggact atataaaaat     120
g                                                                      121

<210> SEQ ID NO 55
<211> LENGTH: 121
<212> TYPE: DNA
<213> ORGANISM: Allium cepa

<400> SEQUENCE: 55
gaatcgcgaa cctttgaaat ggaggggaac accggtattg gagccgatac ccttctcgcc      60
ggtacaaatc gctctaaaat tctctgccgt tctgggaacg acgtcggcaa agagctcaat     120
g                                                                      121

<210> SEQ ID NO 56
<211> LENGTH: 121
<212> TYPE: DNA
<213> ORGANISM: Allium cepa

<400> SEQUENCE: 56
gaatcgcgaa cctttgaaat ggaggggaac accggtattg gagccgatac ccttctcgcc      60
agtacaaatc gctctaaaat tctctgccgt tctgggaacg acgtcggcaa agagctcaat     120
g                                                                      121

<210> SEQ ID NO 57
<211> LENGTH: 121
<212> TYPE: DNA
<213> ORGANISM: Allium cepa
<220> FEATURE:
<221> NAME/KEY: misc_feature
<222> LOCATION: (48)..(48)
<223> OTHER INFORMATION: n is a, c, g, or t

<400> SEQUENCE: 57
agtgctcact gtattatcaa ttccggaagg ttttccatgg ataatctntt caccctcata      60
tgcccatttg tttatgagat caagttcctt ttcccctaaa ttcaaccacc cagattcttt     120
a                                                                      121

<210> SEQ ID NO 58
<211> LENGTH: 121
<212> TYPE: DNA
<213> ORGANISM: Allium cepa
<220> FEATURE:
<221> NAME/KEY: misc_feature
<222> LOCATION: (48)..(48)
```

-continued

```
<223> OTHER INFORMATION: n is a, c, g, or t

<400> SEQUENCE: 58
agtgctcact gtattatcaa ttccggaagg ttttccatgg ataatctntt caccctcata      60
cgcccatttg tttatgagat caagttcctt ttcccctaaa ttcaaccacc cagattcttt     120
a                                                                      121

<210> SEQ ID NO 59
<211> LENGTH: 121
<212> TYPE: DNA
<213> ORGANISM: Allium cepa

<400> SEQUENCE: 59
agttaaaagc acttccacgc ctaggccact atacatatag tccttctcct tcccgttcac      60
gtactccttg cgcctgtaaa aaggaagcac atccagcaca tcttcatttt ccttcagcca     120
c                                                                      121

<210> SEQ ID NO 60
<211> LENGTH: 121
<212> TYPE: DNA
<213> ORGANISM: Allium cepa

<400> SEQUENCE: 60
agttaaaagc acttccacgc ctaggccact atacatatag tccttctcct tcccgttcac      60
atactccttg cgcctgtaaa aaggaagcac atccagcaca tcttcatttt ccttcagcca     120
c                                                                      121

<210> SEQ ID NO 61
<211> LENGTH: 121
<212> TYPE: DNA
<213> ORGANISM: Allium cepa
<220> FEATURE:
<221> NAME/KEY: misc_feature
<222> LOCATION: (1)..(1)
<223> OTHER INFORMATION: n is a, c, g, or t

<400> SEQUENCE: 61
nttaaagagg cctagcgcga gtagttggat cttcattgga ttctactttc atcatgaaaa      60
gatacccaat tatccacaag agcacatatg gaaaaggaat ccagcataaa catgccaata     120
g                                                                      121

<210> SEQ ID NO 62
<211> LENGTH: 121
<212> TYPE: DNA
<213> ORGANISM: Allium cepa
<220> FEATURE:
<221> NAME/KEY: misc_feature
<222> LOCATION: (1)..(1)
<223> OTHER INFORMATION: n is a, c, g, or t

<400> SEQUENCE: 62
nttaaagagg cctagcgcga gtagttggat cttcattgga ttctactttc atcatgaaaa      60
tatacccaat tatccacaag agcacatatg gaaaaggaat ccagcataaa catgccaata     120
g                                                                      121
```

MOLECULAR MARKERS FOR REDUCED PYRUVATE LEVEL TRAIT IN *ALLIUM CEPA*

CROSS-REFERENCE TO RELATED APPLICATIONS

This application is a National Stage Entry of PCT/EP2020/083533, filed Nov. 26, 2020, which claims priority to EP Application No. 20170450.9, filed Apr. 20, 2020, EP Application No. 19216666.8, filed Dec. 16, 2019, and U.S. Provisional Application No. 62/940,667, filed Nov. 26, 2019, the disclosures of each of which are hereby incorporated by reference in their entireties.

FIELD OF THE INVENTION

The present invention relates to the field of plant breeding. Provided is a genetic marker for determining the presence or absence of one or more quantitative trait loci (QTLs) conferring a reduced pyruvate level in an *Allium cepa* plant or plant part, wherein the marker is selected from the group consisting of: a marker linked to a reduced pyruvate conferring QTL located on chromosome 2, a marker linked to a reduced pyruvate conferring QTL located on chromosome 1 and a marker linked to a reduced pyruvate conferring QTL located on chromosome 7. The present invention further relates to the use of the marker of the invention for determining the presence or absence of one or more QTLs conferring a reduced pyruvate level in an *Allium cepa* plant or plant part. The present invention further relates to a method for identifying and/or selecting an *Allium cepa* plant or plant part comprising determining in said plant or plant part the presence or absence of one or more markers of the invention. The present invention relates to isolated nucleic acid and the use of the nucleotide sequences as provided herein for marker assisted selection of an *Allium cepa* plant or plant part.

BACKGROUND

The onion plant is believed to originate from West or Central Asia. In Europe it has been known since the bronze ages. The bulbs of the onion plants, —the "onions"—are used in many dishes and have a very healthy reputation. Plant breeding has been focused on yield, appearance, harvestability, storability, flavour and content as onions contain several compounds that have beneficial effects on health. Some of these compounds are most effective when the onion is consumed fresh and their concentrations are often linked with the solids level of onions. A high solids onion that is mild and sweet enough to be consumed without cooking will deliver more health promoting compounds in the diet.

Pungency is the typical onion flavour or taste, caused by the conversion of sulphur containing flavour precursors—alk(en)yl-L-cysteine-sulfoxides (ACSOs)—by the enzyme alliinase into thiosulfonates when the onion cells are cut or damaged. A by-product of this enzymatic process, pyruvate or pyruvic acid is measured as an indicator of the pungency (Schwimmer and Weston 1961, J. of Agric. Food Chem. 9: 301-4). The amount of pyruvate produced is directly related to onion pungency as determined by taste panels (Schwimmer and Guadagni, 1962, J. Food Sc. 27:94-97).

Pungency is an important commercial trait as consumers favour fresh onions with low pungency and sweet taste. Pungency masks the sweet taste of the sugars, which are present in the onion as part of the water-soluble solids or carbohydrates. Pungency is strongly influenced by the presence or absence of sulphur in the soil or plant nutrients (Randle 1992, Euphytica 59: 151-156 and Randle and Bussard 1993, J. Amer. Soc. Hort. Sci. 118: 766-770), but has also a clear genetic component as shown by Lin (1995, J. Americ. Soc. Hort. Sci. 120: 119-122), Simon (1995, Euphytica 82: 1-8), Wall et al. (1996, Euphytica 87: 133-139) and Wall and Corgan (1999, Euphytica 106: 7-13).

According to some reports (Shock et al. 2004: "Pungency of Selected Onion Varieties Before and After Storage", Oregon State University, Malheur Experiment Station Special Report 1055: 45-46) pungency may significantly increase during storage. There is, therefore, a need for onions which have a reduced pungency at harvest and whereby the pungency does not increase significantly during storage. In particular, there is a need for onions which have a reduced pungency after at least about 2, 3, 4, 5, 6, 7, 8 or more months of storage. Particularly long day onions may be stored, while short day onions are typically consumed after little or no storage. There is especially a need for reduced pungency long day onions whereby the pungency does not increase during storage but remains constant or decreases during storage (compared to the level at harvest), i.e. is lower after at least about 2, 3, 4, 5, 6, 7, 8 or more months of storage compared to the level at harvest. A "decrease during storage" refers, thus, to the level after a specific period of storage (e.g. after about 2, 3, 4, 5, 6, 7, 8 or more months of storage) is lower than at harvest.

Onion plants producing onion bulbs having a reduced pungency have been previously described. WO2007011857A2 describes long day onion plants comprising bulbs having low pungency. WO 2009/092560 A1 describes a long-day onion plant capable of producing onion bulbs comprising an increased content of soluble solids combined with a reduced pungency. EP 2 992 756 A1 describes onion plants in which alliinase gene expression is reduced, wherein amounts of a pungent and a lachrymatory component produced when an onion cell is broken are decreased. One common problem with onion varieties having a reduced pungency is that there may be a reduced consistency with respect to the pungency characteristics. One reason for this is that there is often a large genotype by environment interaction, which can be difficult to genetically fix with phenotypic selection. Further compounding this problem, onion breeding lines are often inbred to the F4 or F5 level before they are "massed" and maintained as a population rather than through single seed decent. This results in residual heterozygosity levels of up to 12.5%. Onion lines accordingly are found to segregate at genetic loci for traits of interest, including loci controlling the pungency trait. In accordance herewith, the development of reliable genetic markers that for determining the presence of reduced pungency alleles has not been successful. With molecular markers for the pungency trait in *Allium cepa* plants available, it may be possible to increase the genetic stability of low pungency lines by fixing these loci in the breeding lines, resulting in more consistent pungency characteristics in the resulting onion varieties. The availability of reliable molecular markers would further allow accelerated breeding of new low pungency varieties as a larger number of individual plants can be screened with molecular markers when compared to more laborious phenotypic screening of pyruvic acid.

SUMMARY OF THE INVENTION

In the current invention, a method for identifying and/or selecting an *Allium cepa* plant or plant part comprising determining the presence or absence of one or more markers suitable for determining the presence of one or more QTLs conferring a reduced pyruvate level in an *Allium cepa* plant or plant part is provided, wherein the marker is selected from the group consisting of: a marker linked to a reduced pyruvate conferring QTL located on chromosome 2 between marker isotig30225_1454 and marker isotig32865_1404, a marker linked to a reduced pyruvate conferring QTL located on chromosome 1 between marker isotig32772_1413 and marker isotig33099_885; and a marker linked to a reduced pyruvate conferring QTL located on chromosome 7 between marker isotig28625_2789 and marker isotig41937_218. The order of the SNP markers identified in the context of the present invention can be derived from Table 7 as provided herein below.

Further provided herein is an isolated nucleic acid comprising the nucleotide sequence selected from the group consisting of: SEQ ID NO: 1 or a fragment thereof consisting of at least 15 nucleotides comprising nucleotide 51 of SEQ ID NO: 1; SEQ ID NO: 3 or a fragment thereof consisting of at least 15 nucleotides comprising nucleotide 51 of SEQ ID NO: 3; SEQ ID NO: 5 or a fragment thereof consisting of at least 15 nucleotides comprising nucleotide 51 of SEQ ID NO: 5; SEQ ID NO: 7 or a fragment thereof consisting of at least 15 nucleotides comprising nucleotide 51 of SEQ ID NO: 7; SEQ ID NO: 9 or a fragment thereof consisting of at least 15 nucleotides comprising nucleotide 51 of SEQ ID NO: 9; SEQ ID NO: 11 or a fragment thereof consisting of at least 15 nucleotides comprising nucleotide 51 of SEQ ID NO: 11; SEQ ID NO: 13 or a fragment thereof consisting of at least 15 nucleotides comprising nucleotide 51 of SEQ ID NO: 13; SEQ ID NO: 15 or a fragment thereof consisting of at least 15 nucleotides comprising nucleotide 51 of SEQ ID NO: 15; SEQ ID NO: 17 or a fragment thereof consisting of at least 15 nucleotides comprising nucleotide 51 of SEQ ID NO: 17; SEQ ID NO: 19, SEQ ID NO: 21 or a fragment thereof consisting of at least 15 nucleotides comprising nucleotide 51 of SEQ ID NO: 21; SEQ ID NO: 23 or a fragment thereof consisting of at least 15 nucleotides comprising nucleotide 51 of SEQ ID NO: 23; SEQ ID NO: 25 or a fragment thereof consisting of at least 15 nucleotides comprising nucleotide 51 of SEQ ID NO: 25; SEQ ID NO: 27 or a fragment thereof consisting of at least 15 nucleotides comprising nucleotide 51 of SEQ ID NO: 27; SEQ ID NO: 29 or a fragment thereof consisting of at least 15 nucleotides comprising nucleotide 51 of SEQ ID NO: 29; SEQ ID NO: 31 or a fragment thereof consisting of at least 15 nucleotides comprising nucleotide 51 of SEQ ID NO: 31; SEQ ID NO: 33 or a fragment thereof consisting of at least 15 nucleotides comprising nucleotide 51 of SEQ ID NO: 33; SEQ ID NO: 35 or a fragment thereof consisting of at least 15 nucleotides comprising nucleotide 51 of SEQ ID NO: 35; SEQ ID NO: 37 or a fragment thereof consisting of at least 15 nucleotides comprising nucleotide 51 of SEQ ID NO: 37; SEQ ID NO: 39 or a fragment thereof consisting of at least 15 nucleotides comprising nucleotide 51 of SEQ ID NO: 39; SEQ ID NO: 41 or a fragment thereof consisting of at least 15 nucleotides comprising nucleotide 51 of SEQ ID NO: 41; SEQ ID NO: 43 or a fragment thereof consisting of at least 15 nucleotides comprising nucleotide 51 of SEQ ID NO: 43; SEQ ID NO: 45 or a fragment thereof consisting of at least 15 nucleotides comprising nucleotide 51 of SEQ ID NO: 45; SEQ ID NO: 47 or a fragment thereof consisting of at least 15 nucleotides comprising nucleotide 51 of SEQ ID NO: 47; and SEQ ID NO: 49 or a fragment thereof consisting of at least 15 nucleotides comprising nucleotide 51 of SEQ ID NO: 49, or comprising the complementary nucleotide sequences thereof.

Also provided herein is the use of one or more of the nucleotide sequences selected from the group consisting of SEQ ID NOs: 1-50 or a fragment thereof for marker assisted selection of an *Allium cepa* plant or plant part, wherein said fragment consists of at least 15 nucleotides comprising nucleotide 51 of said nucleotide sequences selected from the group consisting of SEQ ID NOs: 1-50 or a complementary sequence of said one or more of the nucleotide sequences.

Also provided herein is a marker for identifying an *Allium cepa* plant producing bulbs having a reduced pyruvate level comprising one or more SNPs selected from the group consisting of: SNP_01 comprising a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 on chromosome 2; SNP_02 comprising an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3 on chromosome 2; SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5 on chromosome 2; SNP_04 comprising a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2; SNP_05 comprising a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9 on chromosome 1; SNP_06 comprising an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11 on chromosome 1; SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13 on chromosome 1; SNP_08 comprising a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15 on chromosome 1; SNP_09 comprising a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17 on chromosome 7; SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7; SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 on chromosome 2; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23 on chromosome 2; SNP_13 comprising a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25 on chromosome 2; SNP_14 comprising an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27 on chromosome 2; SNP_15 comprising a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO: 29 on chromosome 2; SNP_16 comprising an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 on chromosome 1; SNP_17 comprising an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33 on chromosome 1; SNP_18 comprising a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35 on chromosome 1; SNP_19 comprising a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37 on chromosome 1; SNP_20 comprising a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1; SNP_21 comprising a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41 on chromosome 1; SNP_22 comprising a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 on chromosome 7; SNP_23 comprising a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45 on chromosome 7; SNP_24 comprising a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47 on chromosome 7; and SNP_25 comprising a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49 on chromosome 7.

BRIEF DESCRIPTION OF THE SEQUENCE LISTING

SEQ ID NO: 1 shows the reduced pungency genotype of SNP_01.

SEQ ID NO: 2 shows the high pungency genotype of SNP_01.

SEQ ID NO: 3 shows the reduced pungency genotype of SNP_02.

SEQ ID NO: 4 shows the high pungency genotype of SNP_02.

SEQ ID NO: 5 shows the reduced pungency genotype of SNP_03.

SEQ ID NO: 6 shows the high pungency genotype of SNP_03.

SEQ ID NO: 7 shows the reduced pungency genotype of SNP_04.

SEQ ID NO: 8 shows the high pungency genotype of SNP_04.

SEQ ID NO: 9 shows the reduced pungency genotype of SNP_05.

SEQ ID NO: 10 shows the high pungency genotype of SNP_05.

SEQ ID NO: 11 shows the reduced pungency genotype of SNP_06.

SEQ ID NO: 12 shows the high pungency genotype of SNP_06.

SEQ ID NO: 13 shows the reduced pungency genotype of SNP_07.

SEQ ID NO: 14 shows the high pungency genotype of SNP_07.

SEQ ID NO: 15 shows the reduced pungency genotype of SNP_08.

SEQ ID NO: 16 shows the high pungency genotype of SNP_08.

SEQ ID NO: 17 shows the reduced pungency genotype of SNP_09.

SEQ ID NO: 18 shows the high pungency genotype of SNP_09.

SEQ ID NO: 19 shows the reduced pungency genotype of SNP_10.

SEQ ID NO: 20 shows the high pungency genotype of SNP_10.

SEQ ID NO: 21 shows the reduced pungency genotype of SNP_11.

SEQ ID NO: 22 shows the high pungency genotype of SNP_11.

SEQ ID NO: 23 shows the reduced pungency genotype of SNP_12.

SEQ ID NO: 24 shows the high pungency genotype of SNP_12.

SEQ ID NO: 25 shows the reduced pungency genotype of SNP_13.

SEQ ID NO: 26 shows the high pungency genotype of SNP_13.

SEQ ID NO: 27 shows the reduced pungency genotype of SNP_14.

SEQ ID NO: 28 shows the high pungency genotype of SNP_14.

SEQ ID NO: 29 shows the reduced pungency genotype of SNP_15.

SEQ ID NO: 30 shows the high pungency genotype of SNP_15.

SEQ ID NO: 31 shows the reduced pungency genotype of SNP_16.

SEQ ID NO: 32 shows the high pungency genotype of SNP_16.

SEQ ID NO: 33 shows the reduced pungency genotype of SNP_17.

SEQ ID NO: 34 shows the high pungency genotype of SNP_17.

SEQ ID NO: 35 shows the reduced pungency genotype of SNP_18.

SEQ ID NO: 36 shows the high pungency genotype of SNP_18.

SEQ ID NO: 37 shows the reduced pungency genotype of SNP_19.

SEQ ID NO: 38 shows the high pungency genotype of SNP_19.

SEQ ID NO: 39 shows the reduced pungency genotype of SNP_20.

SEQ ID NO: 40 shows the high pungency genotype of SNP_20.

SEQ ID NO: 41 shows the reduced pungency genotype of SNP_21.

SEQ ID NO: 42 shows the high pungency genotype of SNP_21.

SEQ ID NO: 43 shows the reduced pungency genotype of SNP_22.

SEQ ID NO: 44 shows the high pungency genotype of SNP_22.

SEQ ID NO: 45 shows the reduced pungency genotype of SNP_23.

SEQ ID NO: 46 shows the high pungency genotype of SNP_23.

SEQ ID NO: 47 shows the reduced pungency genotype of SNP_24.

SEQ ID NO: 48 shows the high pungency genotype of SNP_24.

SEQ ID NO: 49 shows the reduced pungency genotype of SNP_25.

SEQ ID NO: 50 shows the high pungency genotype of SNP_25.

SEQ ID NO: 51 shows the reduced pungency genotype of isotig30225_1454.

SEQ ID NO: 52 shows the high pungency genotype of isotig30225_1454.

SEQ ID NO: 53 shows the reduced pungency genotype of isotig32865_1404.

SEQ ID NO: 54 shows the high pungency genotype of isotig32865_1404.

SEQ ID NO: 55 shows the reduced pungency genotype of isotig32772_1413.

SEQ ID NO: 56 shows the high pungency genotype of isotig32772_1413.

SEQ ID NO: 57 shows the reduced pungency genotype of isotig33099_885.

SEQ ID NO: 58 shows the high pungency genotype of isotig33099_885.

SEQ ID NO: 59 shows the reduced pungency genotype of isotig28625_2789.

SEQ ID NO: 60 shows the high pungency genotype of isotig28625_2789.

SEQ ID NO: 61 shows the reduced pungency genotype of isotig41937_218.

SEQ ID NO: 62 shows the high pungency genotype of isotig41937_218.

DETAILED DESCRIPTION OF THE INVENTION

General Definitions

The term "genome" relates to the genetic material of an organism. It consists of DNA. The genome includes both the genes and the non-coding sequences of the DNA.

The term "genetic determinant" relates to the genetic information in the genome of the plant that causes a particular trait of a plant. Accordingly, a genetic determinant comprises the genetic information (gene or locus or introgression) that confers a certain trait. In general, a genetic determinant may comprise a single gene (or one Quantitative Trait Locus (QTL)) or more than one gene.

"Phenotype" is the observable external and/or physiological appearance of the plant as a result of the interaction between its genotype and its environment. It includes all observable morphological and physiological characteristics and thus encompasses phenotypes such as pungency, PAD measurements and soluble solid contents of onion bulbs.

The word "trait" in the context of this application refers to the phenotype of the plant. When a plant shows the traits of the invention, its genome comprises at least one reduced pungency allele associated with the trait of the invention, particularly in the present invention when the reduced pungency allele is in homozygous form. The plant, thus, has the genetic determinant of the invention. It is understood that when referring to a plant comprising the trait of the plant of the invention, reference is made to an *Allium cepa* plant comprising the trait of reduced pungency as further described herein.

"Genotype" is the total of inheritable genetic information of a plant, partly influenced by the environmental factors, which is expressed in the phenotype.

As used herein, "Onion plant" or "onion" is a plant of the botanical species *Allium cepa* L. or parts thereof, such as the (harvested) bulb, seeds, etc. "Bulb" is the harvested, edible portion of the plant. Onion bulbs may be developing or mature. Herein mature bulbs are preferred, which are bulbs ready for harvest or harvested.

"Long-day" onion plants will initiate bulb formation when light (day length) is at least about 14 contiguous hours or more, e.g., at least about 14, 15 or 16 hours. Preferably this contiguous light (hours per day) is provided for 2, 4, 7, 14, 21, 25 or more days to initiate bulb formation.

"Storage conditions" and "storage" encompass typical conditions used to store (preferably fresh) onions, such as darkness, cool temperature (as used herein, a cool temperature means preferably below 12° C., e.g., about 3-12° C., 3-10° C., 5-10° C. or about 3-5° C., preferably about 3, 4 or 5 degrees Celsius) and a relative humidity (RH) of about 60-80%, preferably about 70-80%, most preferably around 70%. Also preferred is controlled ventilation.

"Soluble Solids" or "Soluble Solids Content" ("SSC" herein), is the percentage (%) of water-soluble compounds in onion bulbs as measured by a refractometer according to the method of Mann and Hoyle, 1945 (Proc. Americ. Soc. Hort. Sci. 46: 285-292) or Foskett and Peterson, 1949 (Proc. Americ. Soc. Hort. Sci. 55: 314-318).

"High SSC" refers herein to an average SSC of a representative number of onion bulbs (e.g., at least 5, 6, 10, 15, 20, 30, 40, 50, 50, 60, 70, 80, 90 or more bulbs) of at least 7.0% or 7.5%, or even at least 8%, 9%, 10%, 11%, 12%, 15%, 20%, 25%, 30% or more. Thus, average SSC of 7.0-30%, 7.5-30%, or even 7.0-20%, 8.0-20%, 7.0-15%, 8.0-15%, 7.0-10%, etc. are encompassed herein.

"Pungency" is the typical sharp taste of onion as the onion bulb tissue disintegrates by comminution. Pungency is preferably determined by measuring the enzymatic development of pyruvic acid according to the method of Schwimmer and Weston (1961, J. of Agric. Food Chemistry 9:301-304), which is strongly correlated to the flavour perception by a test panel (Schwimmer 1962, J. Food Sci. 27: 94-97; Wall and Corgan, 1992, Hort. Science 27: 1029-1030). Alternatively, pyruvic acid, which is also referred to as pyruvate, can be measured using a colorimetric method as described in Anthon and Barrett (2003) Science of Food and Agriculture (83) 1210-1213. Pungency is expressed as µMol (micromoles, also µM or µmol herein) pyruvate per gram fresh weight bulb material (µMol/g FW). It is also referred to as "PAD measurement" (PAD from Pyruvic Acid Develop-ment) or "pyruvate measurement" or "pyruvate level" herein.

The term "reduced pungency" as used herein accordingly refers to a pungency level that is reduced when compared to the pungency level of a reference variety. Preferably, the reduced pungency level corresponds to a pungency level that is reduced to such an extent that the reduced pungency level corresponds to a low pungency level. "Low pungency" refers herein to an average pungency of a representative number of (mature) onion bulbs (e.g., at least about 5, 8, 10, 15, 20, 30, 40, 50, 50, 60, 70, 80, 90 or more bulbs) of less than 5.5 μMol/g FW pyruvate, or even less than 5.0, 4.5, 4.0 μMol/g FW pyruvate, equal to or less than 3.8 or 3.75 μMol/g FW pyruvate, or equal to or less than 3.5, 3.0, 2.5, 2.3, 2.0, 1.8, 1.5, or 1.3 μMol/g FW pyruvate, as determined by PAD measurement. "High pungency" refers herein to an average pungency level of a representative number of (mature) onion bulbs that is higher than the low pungency level as defined herein, preferably more than 5.5 μMol/g FW pyruvate, or even more than 6.0, 6.5, or 7.0 μMol/g FW pyruvate. Pungency can be measured at harvest and/or after 2, 3, 4, 5, 6, 7, 8 or more months of storage.

A "narrow pungency range" refers to the variance in pungency between individual bulbs of a plurality of bulbs obtained from one plant line being narrow, i.e., the pungency level of the most pungent bulb (maximum value) and least pungent bulb (minimum value) differ preferably by less than or at most 5 μMol/g FW pyruvate, more preferably less than or at most 4 μMol/g FW pyruvate or less than or at most 3.5 μMol/g FW pyruvate, more preferably by less than or at most 3.0, 2.5, 2.0, 1.5 or 1.0 μMol/g FW pyruvate. Prefer-ably the maximum pungency (of the most pungent bulb produced by the plant) is equal to or less than 5 μMol/g FW pyruvate, preferably equal to or less than 4.9, 4.8, 4.75, 4.7, 4.5, 4.0 or 3.8, 3.7, 3.5 or 3.0 μMol/g FW pyruvate. Preferably the minimum pungency level (i.e. of the least pungent bulb produced by the plant) is equal to or below 3.0, 2.5, more preferably equal to or below 2.0, 1.3 or 1.2 μMol/g FW pyruvate. Preferred ranges of pungency within a plant line are, thus, that all bulbs have a pungency between 0 (min) and 5 (max) μMol/g FW pyruvate, preferably between 1 (min) and 5 (max) μMol/g FW pyruvate, more preferably between 1 (min) and 4 (max) μMol/g FW pyruvate. Also, in one embodiment of the invention, all bulbs have a pungency between 0 (min) and 5 (max) μMol/g FW pyruvate, prefer-ably between 1 (min) and 5 (max) μMol/g FW pyruvate, more preferably between 1 or 1.2 (min) and 4.9, 4.8, 4.7 or 4.5 (max) μMol/g FW pyruvate, more preferably between 1 (min) and 4 (max) μMol/g FW pyruvate. A narrow pungency range is an important quality characteristic for the consumer. It can be measured at harvest and/or, preferably, after a certain period of storage, e.g. after at least about 2, 3, 4, 5, 6, 7, 8 or more months of storage.

"High pungency allele" refers herein to an allele associ-ated with the high pungency trait as further defined herein. In one embodiment, the high pungency allele is a wild type allele.

"Reduced pungency allele" refers herein to an allele associated with the reduced pungency trait as further defined herein. In one embodiment, the reduced pungency allele is a mutant allele.

"Wild type plant" refers herein to a plant of the species *Allium cepa* producing bulbs having a high pungency as defined herein. Such plants are for example suitable controls in phenotypic essays, particularly if said control plants have the same genetic background as the plants (e.g. low pun-gency plants) that are subjected to phenotypic testing.

"Long storage" refers herein to a storage length of at least 2, 3, 4, 5, 6, 7 or more months. Preferably there is no significant increase in pungency and/or no significant reduc-tion in SSC during the storage period, i.e., when comparing the average pungency and/or SSC at harvest (or shortly after harvest) with the pungency and/or SSC level after 2, 3, 4, 5, 6, 7 or more months of storage. "No significant increase in pungency" refers herein to an increase in pungency mea-surement (i.e., pyruvate) after the storage period by less than 10%, more preferably less than 5%, even more preferably less than 3%, 2% or 1%, more preferably no increase at all, and in one embodiment a reduction in pungency, compared to the measurement at harvest (or shortly after harvest). "No significant reduction in SSC" refers herein to a reduction in SSC levels after the storage period of less than 5%, 4%, 3% or 2%, preferably less than 1% or 0.5%, more preferably unchanged, compared to the SSC level at harvest (or shortly after harvest). In one embodiment the mean SSC level after 2, 3, 4, 5, 6, 7 or more months of storage is at least about 80%, 85%, 87%, 88%, 89%, 90%, 95%, 98% of the level at harvest, more preferably at least about 100%, or 101%, 102%, 103%, 105% of the level at harvest, or more.

A genetic determinant can be inherited in a recessive manner, an intermediate manner, or in a dominant manner. Selection for the phenotypic trait is easier when intermediate or dominant inheritance is involved, as a larger part of the progeny of a cross reveals the trait. In general, a genetic determinant can also comprise a combination of recessive and/or intermediate and/or dominant genes or QTLs.

Selection for a genetic determinant (e.g. a reduced pun-gency allele) can be done on phenotype (the trait that can be observed). Selection can also be done by using molecular genotyping methods, such as one or more molecular markers that are genetically linked to the reduced pungency allele or preferably using the gene or allele sequence itself, e.g. by molecular methods which are able to distinguish between the presence of a reduced pungency allele and wild type allele, or products thereof (such as mRNA or protein encoded by the allele). The use of molecular genotyping methods in breeding (such as "marker assisted selection" when genetically linked markers are used, or other geno-typing methods, such as SNP genotyping) requires a smaller population for screening (when compared to phenotypical selection) and can be done in a very early stage. A further advantage of molecular genotyping methods is the possibil-ity to easily distinguish between homozygous plants or seeds having no copies of any of the high pungency alleles as described herein from plants having one or more copies of one or more of said high pungency alleles, which can be done even before seeds germinate or in early plant devel-opment, e.g. before onion bulbs have developed.

A "plant line" or "breeding line" refers to a plant and its progeny. As used herein, the term "inbred line" refers to a plant line which has been repeatedly selfed and is nearly homozygous for every characteristic. Thus, an "inbred line" or "parent line" refers to a plant which has undergone several generations (e.g. at least 4, 5, 6, 7 or more) of inbreeding, resulting in a plant line with a high uniformity.

The term "allele(s)" means any of one or more alternative forms of a DNA sequence at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (plural loci) means a specific place or places or a site on a chromosome where for example a gene or genetic marker is found. The reduced pungency loci as described herein thus are the locations in the genome of an *Allium cepa* plant where the reduced pungency alleles are found.

The term "linkage group" as used herein is defined as a group of loci that are physically linked together on a single molecule of DNA (a chromosome) and are more often transmitted to progeny together than would be expected according to the law of independent assortment. In the present invention, eight linkage groups were identified. Preferably, each of the eight linkage groups as used herein corresponds to one of the eight chromosomes of the onion genome. Preferably, the term "linkage group 3" as used herein corresponds to chromosome 3 (of *Allium cepa*). Preferably, the term "linkage group 4" as used herein corresponds to chromosome 1 (of *Allium cepa*). Preferably, the term "linkage group 6" as used herein corresponds to chromosome 7 (of *Allium cepa*).

The term "gene" means a (genomic) DNA sequence comprising a region (transcribed region), which is transcribed into a messenger RNA molecule (mRNA) in a cell, and an operably linked regulatory region (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein. A gene may be an endogenous gene (in the species of origin) or a chimeric gene (e.g. a transgene or cisgene). The "promoter" of a gene sequence is defined as a region of DNA that initiates transcription of a particular gene. Promoters are located near the genes they transcribe, on the same strand and upstream on the DNA. Promoters can be about 100-1000 base pairs long. In one aspect the promoter is defined as the region of about 1000 base pairs or more e.g. about 1500 or 2000, upstream of the start codon (i.e. ATG) of the protein encoded by the gene.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment) or which is active itself (e.g. in posttranscriptional gene silencing or RNAi). The coding sequence may be in sense-orientation and encodes a desired, biologically active protein or peptide, or an active peptide fragment.

A "quantitative trait locus", or "QTL" is a chromosomal locus that encodes for one or more alleles that affect the expressivity of a continuously distributed (quantitative) phenotype.

"Physical distance" between loci (e.g. between molecular markers and/or between phenotypic markers) on the same chromosome is the actual physical distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). It is understood that the term "introgression fragment" never includes a whole chromosome, but only a part of a chromosome. The introgression fragment can be large, e.g. even three-quarters or half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2.5 Mb or 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

The term "isogenic plant" refers to two plants which are genetically identical except for the reduced pungency allele of the present invention. In order to investigate the impact of the reduced pungency trait, one can cross a plant line (or variety) of interest with a plant comprising the reduced pungency allele reduced pungency trait and select for progeny expressing the desired trait. Optionally one may have to self the progeny one or more times to be able to determine the genetic determinants for the reduced pungency trait in the plant phenotype. Said progeny can then be backcrossed (at least 2 times, e.g. 3, 4, or preferably 5 or 6 times) with the plant line (or variety) of interest while selecting for progeny having the same phenotype as the plant line (or variety) of interest and expressing the genetic determinants for the reduced pungency trait. The impact of the reduced pungency can then be compared between the plant line (variety) of interest and its isogenic line not comprising the genetic determinants for the reduced pungency trait.

The term "nucleic acid", "nucleic acid sequence", "nucleic acid molecule" or "polynucleotide" are used interchangeably and refer to a DNA or RNA molecule in single or double stranded form, particularly a DNA encoding a protein or protein fragment according to the invention. An "isolated nucleic acid" refers to a nucleic acid which is no longer in the natural environment from which it was isolated, e.g. the nucleic acid in a bacterial host cell or in the plant nuclear or plastid genome.

The terms "protein", "peptide sequence", "amino acid sequence" or "polypeptide" are used interchangeably and refer to molecules consisting of a chain of amino acids, without reference to a specific mode of action, size, 3-dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

An "active protein" or "functional protein" is a protein which has protein activity as measurable in vitro, e.g. by an in vitro activity assay, and/or in vivo, e.g. by the phenotype conferred by the protein. A "wild type" protein is a fully functional protein, as present in the wild type plant. A "mutant protein" is herein a protein comprising one or more mutations in the nucleic acid sequence encoding the protein, whereby the mutation results in (the mutant nucleic acid molecule encoding) a protein having altered activity, preferably a protein having reduced activity, most preferably a protein having no activity.

"Functional derivatives" of a protein as described herein are fragments, variants, analogues, or chemical derivatives of the protein which retain at least a portion of the activity or immunological cross reactivity with an antibody specific for the mutant protein.

A fragment of a mutant protein refers to any subset of the molecule.

Variant peptides may be made by direct chemical synthesis, for example, using methods well known in the art.

An analogue of a mutant protein refers to a non-natural protein substantially similar to either the entire protein or a fragment thereof.

A "mutation" in a nucleic acid molecule is a change of one or more nucleotides compared to the wild type sequence, e.g. by replacement, deletion or insertion of one or more nucleotides.

A "mutation" in an amino acid molecule making up a protein is a change of one or more amino acids compared to the wild type sequence, e.g. by replacement, deletion or insertion of one or more amino acids. Such a protein is then also referred to as a "mutant protein".

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a premature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid at either the N-terminus or the C-terminus of the protein is missing compared to the amino acid sequence of the corresponding wild type protein, whereby in a 3'-end or C-terminal truncation at least the first nucleotide at the 5'-end or the first amino acid at the N-terminus, respectively, is still present and in a 5'-end or N-terminal truncation at least the last nucleotide at the 3'-end or the last amino acid at the C-terminus, respectively, is still present. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made. The "promoter of a gene sequence", accordingly is defined as a region of DNA that initiates transcription of a particular gene. Promoters are located near the genes they transcribe, on the same strand and upstream on the DNA. Promoters can be about 100-1000 base pairs long. In one aspect, the promoter is defined as the region of about 2000 base pairs or more upstream of the start codon (i.e. ATG) of the protein encoded by the gene, preferably, the promoter is the region of about 1500 base pairs upstream of the start codon, more preferably the promoter is the region of about 1000 base pairs upstream of the start codon.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the nucleic acid sequences being linked are typically contiguous.

"Sequence identity" and "sequence similarity" can be determined by alignment of two peptide or two nucleotide sequences using global or local alignment algorithms. Sequences may then be referred to as "substantially identical" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS, (as available on the Internet by ebi.ac.uk at world wide web at ebi.ac.uk under/Tools/psa/emboss_needle/). Alternatively, sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 95%, 96%, 97%, 98%, 98.3%, 98.7%, 99.0%, or 99.3% or more preferably 99.7% (as determined by Emboss "needle" using default parameters, i.e. gap creation penalty=10, gap extension penalty=0.5, using scoring matrix DNAFULL for nucleic acids and Blosum62 for proteins). Such sequences are also referred to as 'variants' herein, e.g. other variants of alleles causing the reduced pungency trait of the present invention and proteins than the specific nucleic acid and amino acid sequences dis-closed herein can be identified, which have the same effect on pungency as the plants of the pre-sent invention.

The term "hybridisation" as used herein is generally used to mean hybridisation of nucleic acids at appropriate conditions of stringency (stringent hybridisation conditions) as would be readily evident to those skilled in the art depending upon the nature of the probe sequence and target sequences. Conditions of hybridisation and washing are well-known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold Spring Harbor Press, Cold Spring Harbor, New York, 1989. The choice of conditions is dictated by the length of the sequences being hybridised, in particular, the length of the probe sequence, the relative G-C content of the nucleic acids and the amount of mismatches to be permitted. Low stringency conditions are preferred when partial hybridisation between strands that have lesser degrees of complementarity is desired. When perfect or near perfect complementarity is desired, high stringency conditions are preferred. For typical high stringency conditions, the hybridisation solution contains 6×S.S.C., 0.01 M EDTA, 1×Denhardt's solution and 0.5% SOS. hybridisation is carried out at about 68° C. for about 3 to 4 hours for fragments of cloned DNA and for about 12 to about 16 hours for total eukaryotic DNA. For lower stringencies the temperature of hybridisation is reduced to about 42° C. below the melting temperature ($T_M$) of the duplex. The $T_M$ is known to be a function of the G-C content and duplex length as well as the ionic strength of the solution.

As used herein, the phrase "hybridizes" to a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridisation under appropriate conditions. For example, a 100 nucleotide long molecule from the 3' coding or non-coding region of a gene will recognize and hybridize to an approximately 100 nucleotide portion of a nucleotide sequence within the 3' coding or non-coding region of that gene or any other plant gene so long as there is about 70% or more sequence similarity between the two sequences. It is to be understood that the size of the corresponding portion will allow for some mismatches in hybridisation such that the corresponding portion may be smaller or larger than the molecule which hybridizes to it, for example 20-30% larger or smaller, preferably no more than about 12-15% larger or smaller.

As used herein, the phrase "a sequence comprising at least 95% sequence identity" or "a sequence comprising at least 95% amino acid sequence identity" or "a sequence comprising at least 95% nucleotide sequence identity" means a sequence having at least 95% e.g. at least 96%, 97%, 98%, 98.3%, 98.7%, 99.0%, or 99.3% or more preferably 99.7% sequence identity when compared with the reference sequence that is indicated. Sequence identity can be determined according the methods described herein.

A "fragment" of the gene or DNA sequence refers to any subset of the molecule, e.g., a shorter polynucleotide or oligonucleotide. In one aspect the fragment comprises the mutation as defined by the invention.

A "variant" of the gene or DNA refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. Preferably the variant comprises the reduced pungency allele as defined by the invention.

As used herein, the term "plant" includes the whole plant or any parts or derivatives thereof, such as plant organs (e.g., harvested or non-harvested flowers, leaves, bulbs, etc.), plant cells, plant protoplasts, plant cell or tissue cultures from which whole plants can be regenerated, regenerable or non-regenerable plant cells, plant calli, plant cell clumps, and plant cells that are intact in plants, or parts of plants, such as embryos, pollen, ovules, ovaries (e.g., harvested tissues or organs), flowers, leaves, seeds, bulbs, clonally propagated plants, roots, stems, cotyledons, hypocotyls, root tips and the like. Also any developmental stage is included, such as seedlings, immature and mature, etc. Preferably, the plant part or derivative comprises the gene or locus as defined by the current invention.

A "plant line" or "breeding line" refers to a plant and its progeny.

"Plant variety" or "variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of 1 locus or gene (or a series of phenotypical characteristics due to this single locus or gene), but which can otherwise differ from one another enormously as regards the other loci or genes. "F1, F2, etc." refers to the consecutive related generations following a cross between two parent plants or parent lines. The plants grown from the seeds produced by crossing two plants or lines is called the F1 generation. Selfing the F1 plants results in the F2 generation, etc. "F1 hybrid" plant (or F1 seed, or hybrid) is the generation obtained from crossing two inbred parent lines. "Selfing", accordingly, refers to the self-pollination of a plant, i.e. to the union of gametes from the same plant.

"Backcrossing" refers to a breeding method by which a (single) trait, such as the capability for inducing a decreased pungency, can be transferred from one genetic background (also referred to as "donor" generally, but not necessarily, this is an inferior genetic background) into another genetic background (also referred to as "recurrent parent"; generally, but not necessarily, this is a superior genetic background). An offspring of a cross (e.g. an F1 plant obtained by crossing a first plant of a certain plant species comprising the reduced pungency allele of the present invention with a second plant of the same plant species or of a different plant species that can be crossed with said first plant species wherein said second plant species does not comprise the reduced pungency allele of the present invention; or an F2 plant or F3 plant, etc., obtained by selfing the F1) is "backcrossed" to a parent plant of said second plant species. After repeated backcrossing, the trait of the donor genetic background, e.g. the reduced pungency allele conferring reduced pungency trait of the present invention, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes transferred from the donor parent. The plants grown from the seeds produced by backcrossing of the F1 plants with the second parent plant line is referred to as the "BC1 generation". Plants from the BC1 population may be selfed resulting in the BC1F2 generation or backcrossed again with the cultivated parent plant line to provide the BC2 generation. An "M1 population" is a plurality of mutagenized seeds/plants of a certain plant line. "M2, M3, M4, etc." refers to the consecutive generations obtained following selfing of a first mutagenized seed/plant (M1).

The term "cultivated plant" or "cultivar" refers to plants of a given species, e.g. varieties, breeding lines or cultivars of the said species, cultivated by humans and having good agronomic characteristics. The so-called heirloom varieties or cultivars, i.e. open pollinated varieties or cultivars commonly grown during earlier periods in human history and often adapted to specific geographic regions, are in one aspect of the invention encompassed herein as cultivated plants. The term "cultivated plant" does not encompass wild plants. "Wild plants" include for example wild accessions.

The term "food" is any substance consumed to provide nutritional support for the body. It is usually of plant or animal origin, and contains essential nutrients, such as carbohydrates, fats, proteins, vitamins, or minerals. The substance is ingested by an organism and assimilated by the organism's cells in an effort to produce energy, maintain life, or stimulate growth. The term food includes substance consumed to provide nutritional support for both the human and animal body.

Throughout this document "average" and "mean" are used interchangeably and refer to the arithmetic mean.

It is understood that comparisons between different plant lines involves growing a number of plants of a line (or variety) (e.g. at least 5 plants, preferably at least 10 plants per line) under the same conditions as the plants of one or more control plant lines (preferably wild type plants) and the determination of differences, preferably statistically significant differences, between the plant lines when grown under the same environmental conditions. Preferably the plants are of the same line or variety.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". It is further understood that, when referring to "sequences" herein, generally the actual physical molecules with a certain sequence of subunits (e.g. amino acids or nucleic acids) are referred to.

Markers and Use Thereof

The present invention provides a marker for identifying an *Allium cepa* plant producing bulbs having a reduced pyruvate level comprising wherein the marker is selected from the group consisting of: a marker linked to a reduced pyruvate conferring QTL located on chromosome 2 between marker isotig30225_1454 and marker isotig32865_1404; a marker linked to a reduced pyruvate conferring QTL located on chromosome 1 between marker isotig32772_1413 and marker isotig33099_885; and a marker linked to a reduced pyruvate conferring QTL located on chromosome 7 between marker isotig28625_2789 and marker isotig41937_218. The marker of the present invention is particularly useful for determining the presence or absence of one or more QTLs conferring a reduced pyruvate level in an *Allium cepa* plant or plant part as described in WO 2009/092560 A1. In one embodiment, accordingly, the present invention provides a marker suitable for determining the presence of one or more QTLs conferring a reduced pyruvate level in an *Allium cepa* plant or plant part wherein the one or more QTLs conferring a reduced pyruvate level is or are as present in a plant of which seeds were deposited under Accession No. PTA-9053, a plant of which seeds were deposited under Accession No. PTA9054 or a plant of which seeds were deposited under Accession No. PTA-9055. In one embodiment, accordingly, the present invention provides a marker suitable for determining the presence of one or more QTLs conferring a reduced pyruvate level in an *Allium cepa* plant or plant part obtained by crossing a plant of which seeds were deposited under Accession No. PTA-9053, a plant of which seeds were deposited under Accession No. PTA9054 or a plant of which seeds were deposited under Accession No. PTA-9055 with another onion plant, wherein the marker is selected from the group consisting of: a marker linked to a reduced pyruvate conferring QTL located on chromosome 2 between marker isotig30225_1454 and marker isotig32865_1404; a marker linked to a reduced pyruvate conferring QTL located on chromosome 1 between marker isotig32772_1413 and marker isotig33099_885; and a marker linked to a reduced pyruvate conferring QTL located on chromosome 7 between marker isotig28625_2789 and marker isotig41937_218.

The publicly available genetic markers isotig30225_1454 and isotig32865_1404 as located on map B9885×B8667 of chromosome 2 are well-known in the art and are described in more detail in Munaiz and Havey (2020) J. Amer. Soc. Hort. Sci., 145(1), 67-72. The publicly available genetic markers isotig32772_1413 and isotig33099_885 as located on map Char×B5351 of chromosome 1 are well-known in the art and are described in more detail in Havey (2000) J. Amer. Soc. Hort. Sci., 145(2), 110-119. The publicly available genetic markers isotig28625_2789 and isotig41937_218 as located on map B9885×B8667 of chromosome 7 are well-known in the art and are described in more detail in Munaiz and Havey (2020) J. Amer. Soc. Hort. Sci., 145(1), 67-72. All of the publicly available genetic markers as referenced here are furthermore detailed in Duangjit et al. (2013) Theor Appl Genet 126, 2093-2101. The nucleotide sequences of these publicly available genetic markers are further described in Table 5.

Preferably, the present invention provides a marker for identifying an *Allium cepa* plant producing bulbs having a reduced pyruvate level comprising one or more SNPs selected from the group consisting of: SNP_01 comprising a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 on chromosome 2; SNP_02 comprising an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3 on chromosome 2; SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5 on chromosome 2; SNP_04 comprising a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2; SNP_05 comprising a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9 on chromosome 1; SNP_06 comprising an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11 on chromosome 1; SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13 on chromosome 1; SNP_08 comprising a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15 on chromosome 1; SNP_09 comprising a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17 on chromosome 7; SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7; SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 on chromosome 2; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23 on chromosome 2; SNP_13 comprising a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25 on chromosome 2; SNP_14 comprising an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27 on chromosome 2; SNP_15 comprising a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO: 29 on chromosome 2; SNP_16 comprising an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 on chromosome 1; SNP_17 comprising an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33 on chromosome 1; SNP_18 comprising a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35 on chromosome 1; SNP_19 comprising a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37 on chromosome 1; SNP_20 comprising a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1; SNP_21 comprising a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41 on chromosome 1; SNP_22 comprising a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 on chromosome 7; SNP_23 comprising a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45 on chromosome 7; SNP_24 comprising a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47 on chromosome 7; and SNP_25 comprising a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49 on chromosome 7.

A "marker", or a "genetic marker" is a DNA fragment with a known location on a chromosome that is polymorphous between individuals (e.g. individual plants that form part of a plant population) that can be used to distinguish and/or identify individuals from the other. In one embodiment, the reduced pyruvate conferring QTL is located between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2. The skilled person can readily identify one or more suitable genetic markers that are linked to the reduced pyruvate conferring QTL as located at the herein defined locus of chromosome 2 (i.e. between marker isotig30225_1454 and marker isotig32865_1404 and/or between SNP_11 and SNP_4 as further defined herein) using conventional methods. In one embodiment, the reduced pyruvate conferring QTL is located between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1. The skilled person can readily identify one or more suitable genetic markers that are linked to the reduced pyruvate conferring QTL as located at the herein defined locus of chromosome 1 (i.e. between marker isotig32772_1413 and marker isotig33099_885 and/or between SNP_16 and SNP_20 as further defined herein) using conventional methods. In one embodiment, the reduced pyruvate conferring QTL is located between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7. The skilled person can readily identify one or more suitable genetic markers that are linked to the reduced pyruvate conferring QTL as located at the herein defined locus of chromosome 7 (i.e. between marker isotig28625_2789 and marker isotig41937_218 and/or between SNP_22 and the distal end of chromosome 7 that includes SNP_10 as further defined herein) using conventional methods. As used herein when referring to the term "marker that is linked" it is specifically meant that the "marker is genetically linked".

The present invention accordingly provides a marker for determining the presence or absence of one or more QTLs conferring a reduced pyruvate level in an *Allium cepa* plant or plant part, wherein the marker is selected from the group consisting of: a marker linked to a reduced pyruvate conferring QTL located on chromosome 2 between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7, a marker linked to a reduced pyruvate conferring QTL located on chromosome 1 between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and a marker linked to a reduced pyruvate conferring QTL located on chromosome 7 between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

Despite the residual heterozygosity present in the initially available low pungency onion lines, the inventors succeeded in the identification of three significant QTLs conferring a reduced pyruvate level in bulbs produced by onion plants. Before the QTLs according to the present invention could be identified, various technical difficulties had to be overcome. The construction of the multiple mapping populations required careful planning, with parental plants for populations being grown almost six years before materials were available for QTL analysis. Because the mechanism of low pyruvate was unknown in the low pyruvate donor, several crosses were made. The results showed that the low pyruvate trait was a complex trait under the control of at least three genetic loci, and it was necessary to construct and analyse multiple mapping populations to identify the three QTLs in the present invention, as there were no redundant QTL detected in the two populations. Validation of the QTLs also required a nonconventional approach, due again to the long generation time of onion. Aside from the challenges relating to the actual mapping and validation, significant work was required prior to these efforts to develop genome wide molecular markers to enable genetic mapping, as well as the development through phenotypic selection of a low pyruvate donor line, which took several decades of directed breeding. One reduced pyruvate conferring QTL was identified on linkage group 3 located between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7. A further reduced pyruvate conferring QTL was identified on linkage group 4 between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39. Yet a further reduced pyruvate conferring QTL was identified on linkage group 6 between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of linkage group 6 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

It was found that linkage group 3 corresponds to chromosome 2 of *Allium cepa*, linkage group 4 corresponds to chromosome 1 of *Allium cepa* and linkage group 6 corresponds to chromosome 7 of *Allium cepa*. The term "linkage group 3" as used herein thus corresponds to the term "chromosome 2". The term "linkage group 4" as used herein thus corresponds to the term "chromosome 1". The term "linkage group 6" as used herein thus corresponds to the term "chromosome 7". The present invention accordingly provides a marker for determining the presence or absence of one or more QTLs conferring a reduced pyruvate level in an *Allium cepa* plant or plant part, wherein the marker is selected from the group consisting of: a marker linked to a reduced pyruvate conferring QTL located on chromosome 2 between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7, a marker linked to a reduced pyruvate conferring QTL located on chromosome 1 between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 51; and a marker linked to a reduced pyruvate conferring QTL located on chromosome 7 between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

Preferably, the present invention provides a marker for determining the presence or absence of one or more QTLs conferring a reduced pyruvate level in an *Allium cepa* plant or plant part, wherein the marker is selected from the group consisting of: a marker linked to a reduced pyruvate conferring QTL located on chromosome 2 between SNP_01 located at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 and SNP_04 located at nucleotide 51 of SEQ ID NO: 7 or at nucleotide 51 of a sequence comprising at least 95% (at least 98% or at least 99%) identity to SEQ ID NO: 7, a marker linked to a reduced pyruvate conferring QTL located on chromosome 1 between SNP_16 located at nucleotide 51 of SEQ ID NO: 31 or at nucleotide 51 of a sequence comprising at least 95% (at least 98% or at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and a marker linked to a reduced pyruvate conferring QTL located on chromosome 7 between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19. The present invention accordingly provides markers for determining the presence or absence of one or more of said QTLs conferring a reduced pyruvate level in an *Allium cepa* plant or plant part. Such a marker, also named herein as a "molecular marker", may be any measurable indicator that is genetically linked to the trait of interest, in the context of the present invention accordingly a reduced pungency allele. Particularly preferred in the context of the present invention is a DNA-based marker including, but not limited to: a restriction fragment length polymorphism (RFLP) marker, a cleaved amplified polymorphic sequence (CPAS) marker, a microsatellite marker (also known as short tandem repeats (STRs) or simple sequence repeats (SSRs), a restriction fragment length polymorphism (RFLP) marker, a random amplification of polymorphic DNA (RAPD) marker, an amplified fragment length polymorphism (AFLP) marker, and a single nucleotide polymorphism (SNP) marker. Preferably, the marker according to the present invention is a SNP marker.

Different specific SNP markers that are linked to a reduced pyruvate conferring QTL located on chromosome 2 were also identified in the context of the present invention. Such a specific SNP marker linked to a reduced pyruvate conferring QTL located on chromosome 2 is selected from the group consisting of: SNP_11 located at nucleotide 51 of SEQ ID NO: 21 or at nucleotide 51 of a sequence comprising at least 95% (at least 98% or at least 99%) identity to SEQ ID NO: 21; SNP_12 located at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 located at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 located at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 located at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 located at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_3 located at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7; and SNP_15 located at nucleotide 51 of SEQ ID NO: 29 or at nucleotide 51 of a sequence comprising at least 95% (more preferably at least 96%, at least 97%, at least 98% or even at least 99%) identity to SEQ ID NO: 29. Accordingly, specific examples for a SNP marker suitable for determining the presence or absence of a reduced pyruvate conferring QTL located on chromosome 2 between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 are: SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 located at nucleotide 51 of SEQ ID NO: 23 or at nucleotide 51 of a sequence comprising at least 95% (more preferably at least 96%, at least 97%, at least 98% or even at least 99%)

identity to SEQ ID NO: 23; SNP_13 located at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 located at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 located at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 located at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_3 located at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7; and SNP_15 located at nucleotide 51 of SEQ ID NO: 29 or at nucleotide 51 of a sequence comprising at least 95% (more preferably at least 96%, at least 97%, at least 98% or even at least 99%) identity to SEQ ID NO: 29. Preferably, a specific SNP marker linked to a reduced pyruvate conferring QTL located on chromosome 2 is selected from the group consisting of: SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 located at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 located at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 located at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 located at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 located at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_3 located at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7. Accordingly, specific examples for a SNP marker suitable for determining the presence or absence of a reduced pyruvate conferring QTL located on chromosome 2 between marker isotig30225_1454 and marker isotig32865_1404 (preferably between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7) are: SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 located at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 located at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 located at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 located at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 located at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_3 located at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7. The SNP marker linked to a reduced pyruvate conferring QTL located on chromosome 2 thus may be useful for determining the presence of a QTL conferring a reduced pyruvate level, wherein: SNP_11 comprises an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 comprises a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 comprises a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 comprises an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 comprises a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 comprises an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_03 comprises a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; SNP_04 comprises a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7; and SNP_15 comprises a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO:29. Preferably, the SNP marker linked to a reduced pyruvate conferring QTL located on chromosome 2 thus may be useful for determining the presence of a QTL conferring a reduced pyruvate level, wherein: SNP_11 comprises an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 comprises a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 comprises a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25; SNP_14 comprises an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27; SNP_01 comprises a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1; SNP_02 comprises an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3; SNP_03 comprises a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; and SNP_04 comprises a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7.

Different specific SNP markers that are linked to a reduced pyruvate conferring QTL located on chromosome 1 were also identified in the context of the present invention. Such a SNP marker linked to a reduced pyruvate conferring QTL located on chromosome 1 is selected from the group consisting of: SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 located at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 located at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 located at nucleotide 51 of SEQ ID NO: 11 or at nucleotide 51 of a sequence comprising at least 95% (more preferably at least 96%, at least 97%, at least 98% or even at least 99%) identity to SEQ ID NO: 11; SNP_7 located at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 located at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 located at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 located at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and SNP_21 located at nucleotide 51 of SEQ ID NO: 41 or at nucleotide 51 of a sequence comprising at least 95% (more preferably at least 96%, at least 97%, at least 98% or even at least 99%) identity to SEQ ID NO: 51. Accordingly, specific examples for a SNP marker suitable for determining the presence or absence of a reduced pyruvate conferring QTL located on chromosome 1 between marker isotig32772_1413 and marker isotig33099_885 (preferably between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39) are: SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 located at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 located at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 located at nucleotide 51 of SEQ ID NO: 11 or at nucleotide 51 of a sequence comprising at least 95% (more preferably at least 96%, at least 97%, at least 98% or even at least 99%) identity to SEQ ID NO:11; SNP_7 located at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 located at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 located at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 located at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and SNP_21 located at nucleotide 51 of SEQ ID NO: 41 or at nucleotide 51 of a sequence comprising at least 95% (more preferably at least 96%, at least 97%, at least 98% or even at least 99%) identity to SEQ ID NO: 41. Preferably, a SNP marker linked to a reduced pyruvate conferring QTL located on chromosome 1 is selected from the group consisting of: SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 located at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 located at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 located at nucleotide 51 of SEQ ID NO: 11 or at nucleotide 51 of a sequence comprising at least 95% (more preferably at least 96%, at least 97%, at least 98% or even at least 99%) identity to SEQ ID NO: 11; SNP_7 located at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 located at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 located at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 located at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and SNP_21 located at nucleotide 51 of SEQ ID NO: 41 or at nucleotide 51 of a sequence comprising at least 95% (more preferably at least 96%, at least 97%, at least 98% or even at least 99%) identity to SEQ ID NO: 41. Accordingly, specific examples for a SNP marker suitable for determining the presence or absence of a reduced pyruvate conferring QTL located on chromosome 1 between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 are: SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 located at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 located at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 located at nucleotide 51 of SEQ ID NO: 11 or at nucleotide 51 of a sequence comprising at least 95% (more preferably at least 96%, at least 97%, at least 98% or even at least 99%) identity to SEQ ID NO: 11; SNP_7 located at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 located at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 located at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 located at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39. The SNP marker linked to a reduced pyruvate conferring QTL located on chromosome 1 thus may be useful for determining the presence of a QTL conferring a reduced pyruvate level, wherein: SNP_16 comprises an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 comprises an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 comprises a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 comprises an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11; SNP_07 comprises a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 comprises a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 comprises a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 comprises a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; SNP_20 comprises a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and SNP_21 comprises a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41. Preferably, the SNP marker linked to a reduced pyruvate conferring QTL located on chromosome 1 thus may be useful for determining the presence of a QTL conferring a reduced pyruvate level, wherein: SNP_16 comprises an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31; SNP_17 comprises an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33; SNP_05 comprises a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9; SNP_06 comprises an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11; SNP_07 comprises a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13; SNP_08 comprises a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15; SNP_18 comprises a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35; SNP_19 comprises a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37; and SNP_20 comprises a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39.

Different specific SNP markers that are linked to a reduced pyruvate conferring QTL located on chromosome 7 were also identified in the context of the present invention. Such a SNP marker linked to a reduced pyruvate conferring QTL located on chromosome 7 is selected from the group consisting of: SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43; SNP_23 located at nucleotide 51 of SEQ ID NO: 45 or at nucleotide 51 of a sequence comprising at least 95% (more preferably at least 96%, at least 97%, at least 98% or even at least 99%) identity to SEQ ID NO: 45; SNP_24 located at nucleotide 51 of SEQ ID NO: 47 or at nucleotide 51 of a sequence comprising at least 95% (more preferably at least 96%, at least 97%, at least 98% or even at least 99%) identity to SEQ ID NO: 47; SNP_25 located at nucleotide 51 of SEQ ID NO: 49 or at nucleotide 51 of a sequence comprising at least 95% (more preferably at least 96%, at least 97%, at least 98% or even at least 99%) identity to SEQ ID NO: 49; SNP_09 located at nucleotide 51 of SEQ ID NO: 17 or at nucleotide 51 of a sequence comprising at least 95% (more preferably at least 96%, at least 97%, at least 98% or even at least 99%) identity to SEQ ID NO: 17; and SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19. Accordingly, specific examples for a SNP marker suitable for determining the presence or absence of a reduced pyruvate conferring QTL located on chromosome 7 between marker isotig28625_2789 and marker isotig41937_218 (preferably between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19) are:

SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43; SNP_23 located at nucleotide 51 of SEQ ID NO: 45 or at nucleotide 51 of a sequence comprising at least 95% (more preferably at least 96%, at least 97%, at least 98% or even at least 99%) identity to SEQ ID NO: 45; SNP_24 located at nucleotide 51 of SEQ ID NO: 47 or at nucleotide 51 of a sequence comprising at least 95% (more preferably at least 96%, at least 97%, at least 98% or even at least 99%) identity to SEQ ID NO: 47; SNP_25 located at nucleotide 51 of SEQ ID NO: 49 or at nucleotide 51 of a sequence comprising at least 95% (more preferably at least 96%, at least 97%, at least 98% or even at least 99%) identity to SEQ ID NO: 49; SNP_09 located at nucleotide 51 of SEQ ID NO: 17 or at nucleotide 51 of a sequence comprising at least 95% (more preferably at least 96%, at least 97%, at least 98% or even at least 99%) identity to SEQ ID NO: 17; and SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19. The SNP marker linked to a reduced pyruvate conferring QTL located on chromosome 7 thus may be useful for determining the presence of a QTL conferring a reduced pyruvate level, wherein: SNP_22 comprises a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43; SNP_23 comprises a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45; SNP_24 comprises a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47; SNP_25 comprises a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49; SNP_09 comprises a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17; and SNP_10 comprises a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

The markers according to the present invention preferably are selected from the group consisting of: a marker linked to a reduced pyruvate conferring QTL located on chromosome 2 between marker isotig30225_1454 and marker isotig32865_1404 (preferably between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7), a marker linked to a reduced pyruvate conferring QTL located on chromosome 1 between marker isotig32772_1413 and marker isotig33099_885 (preferably between SNP_16 located at nucleotide 51 of SEQ ID NO: 31 or at nucleotide 51 of a sequence comprising at least 95%

(more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39); and a marker linked to a reduced pyruvate conferring QTL located on chromosome 7 between marker isotig28625_2789 and marker isotig41937_218 (preferably between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19) thus are particularly useful for determining the presence or absence of one or more QTLs conferring a reduced pyruvate level in an *Allium cepa* plant or plant part.

The present invention accordingly provides a marker for identifying an *Allium cepa* plant producing bulbs having a reduced pyruvate level comprising one or more SNPs selected from the group consisting of: SNP_01 comprising a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 on chromosome 2; SNP_02 comprising an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3 on chromosome 2; SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5 on chromosome 2; SNP_04 comprising a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2; SNP_05 comprising a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9 on chromosome 1; SNP_06 comprising an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11 on chromosome 1; SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13 on chromosome 1; SNP_08 comprising a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15 on chromosome 1; SNP_09 comprising a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17 on chromosome 7; SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7; SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 on chromosome 2; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23 on chromosome 2; SNP_13 comprising a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25 on chromosome 2; SNP_14 comprising an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27 on chromosome 2; SNP_15 comprising a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO: 29 on chromosome 2; SNP_16 comprising an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 on chromosome 1; SNP_17 comprising an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33 on chromosome 1; SNP_18 comprising a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35 on chromosome 1; SNP_19 comprising a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37 on chromosome 1; SNP_20 comprising a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1; SNP_21 comprising a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41 on chromosome 1; SNP_22 comprising a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 on chromosome 7; SNP_23 comprising a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45 on chromosome 7; SNP_24 comprising a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47 on chromosome 7; and SNP_25 comprising a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49 on chromosome 7.

Methods of Identifying and/or Selecting a Plant or Plant Part

The present invention provides a method for identifying and/or selecting an *Allium cepa* plant or plant part comprising determining in said plant or plant part the presence or absence of one or more markers as described herein. Accordingly, the present invention provides a method for identifying and/or selecting an *Allium cepa* plant or plant part comprising determining in said plant or plant part the presence or absence of one or more markers suitable for determining the presence of one or more QTLs conferring a reduced pyruvate level in an *Allium cepa* plant or plant part, wherein the marker is selected from the group consisting of: a marker linked to a reduced pyruvate conferring QTL located on chromosome 2 between marker isotig30225_1454 and marker isotig32865_1404; a marker linked to a reduced pyruvate conferring QTL located on chromosome 1 between marker isotig32772_1413 and marker isotig33099_885; and a marker linked to a reduced pyruvate conferring QTL located on chromosome 7 between marker isotig28625_2789 and marker isotig41937_218.

The method for identifying and/or selecting an *Allium cepa* plant or plant part of the present invention is particularly useful for determining the presence or absence of one or more QTLs conferring a reduced pyruvate level in an *Allium cepa* plant or plant part as described in WO 2009/ 092560 A1. In one embodiment, accordingly, the present invention provides a method for identifying and/or selecting an *Allium cepa* plant or plant part comprising determining in said plant or plant part the presence or absence of one or more markers suitable for determining the presence of one or more QTLs conferring a reduced pyruvate level in an *Allium cepa* plant or plant part wherein the one or more QTLs conferring a reduced pyruvate level is or are as present in a plant of which seeds were deposited under Accession No. PTA-9053, a plant of which seeds were deposited under Accession No. PTA9054 or a plant of which seeds were deposited under Accession No. PTA-9055. In one embodiment, accordingly, the present invention provides a method for identifying and/or selecting an *Allium cepa* plant or plant part comprising determining in said plant or plant part the presence or absence of one or more markers suitable for determining the presence of one or more QTLs conferring a reduced pyruvate level in an *Allium cepa* plant or plant part obtained by crossing a plant of which seeds were deposited under Accession No. PTA-9053, a plant of which seeds were deposited under Accession No. PTA9054 or a plant of which seeds were deposited under Accession No. PTA-9055 with another onion plant, wherein the marker is selected from the group consisting of: a marker linked to a reduced pyruvate conferring QTL located on chromosome 2 between marker isotig30225_1454 and marker isotig32865_1404; a marker linked to a reduced pyruvate conferring QTL located on chromosome 1 between marker isotig32772_1413 and marker isotig33099_885; and a marker linked to a reduced pyruvate conferring QTL located on chromosome 7 between marker isotig28625_2789 and marker isotig41937_218.

Preferably, the present invention provides a method for identifying and/or selecting an *Allium cepa* plant or plant part comprising determining in said plant or plant part the presence or absence of one or more markers suitable for determining the presence of one or more QTLs conferring a reduced pyruvate level in an *Allium cepa* plant or plant part, wherein the marker is selected from the group consisting of: a marker linked to a reduced pyruvate conferring QTL located on chromosome 2 between SNP_11 located at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 and SNP_04 located at nucleotide 51 of SEQ ID NO: 7 or at nucleotide 51 of a sequence comprising at least 95% (more preferably at least 96%, at least 97%, at least 98% or even at least 99%) identity to SEQ ID NO: 7, a marker linked to a reduced pyruvate conferring QTL located on chromosome 1 between SNP_16 located at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 and SNP_20 located at nucleotide 51 of SEQ ID NO: 39 or at nucleotide 51 of a sequence comprising at least 95% (more preferably at least 96%, at least 97%, at least 98% or even at least 99%) identity to SEQ ID NO: 39; and a marker linked to a reduced pyruvate conferring QTL located on chromosome 7 between SNP_22 located at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 and the distal end of chromosome 7 that includes SNP_10 located at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

Preferably, the method comprises screening at the DNA, RNA (or cDNA) or protein level using known methods, in order to detect the presence or absence of one or more QTLs conferring a reduced pyruvate level in an *Allium cepa* plant or plant as described herein. There are many methods to detect presence or absence of the reduced pungency allele of the present invention.

For example, there may be a single nucleotide polymorphism (SNP) between the wild type allele and the reduced pungency allele, a SNP genotyping assay can be used to detect whether a plant or plant part or cell comprises one or more of the wild type (high pungency) nucleotides or the reduced pungency nucleotides in its genome. For example, the one or more SNPs can easily be detected using a KASP assay, for example 50 base pairs upstream and 50 base pairs downstream of the SNP can be selected and two allele-specific forward primers and one allele specific reverse primer can be designed; see e.g. Allen et al. (2011) Plant Biotechnology J 9, 1086-1099, especially p 1097-1098 for a KASP assay method.

Equally, other genotyping assays can be used. For example, a TaqMan SNP genotyping assay, a High Resolution Melting (HRM) assay, SNP genotyping arrays (e.g. Fluidigm, Illumina, etc.) or DNA sequencing may equally be used.

Molecular markers may also be used to aid in the identification of the plants (or plant parts or nucleic acids obtained therefrom) containing the reduced pungency allele. For example, one can develop one or more suitable molecular markers which are closely genetically (and preferably also physically) linked to the reduced pungency allele. Most preferably, the causal gene mutation is used as the molecular marker used for the identification of the plants (or plant parts or nucleic acids obtained therefrom) containing the reduced pungency allele. Suitable molecular markers can be developed by crossing an *Allium cepa* plant having the reduced pungency trait with a wild type plant and developing a segregating population (e.g. F2 or backcross population) from that cross. The segregating population can then be phenotyped for the reduced pungency phenotype and genotyped using e.g. molecular markers such as SNPs (Single Nucleotide Polymorphisms), AFLPs (Amplified Fragment Length Polymorphisms; see, e.g., EP 534 858), or others, and by software analysis molecular markers which co-segregate with the reduced pungency trait in the segregating population can be identified and their order and genetic distance (centimorgan distance, cM) to the reduced pyruvate conferring QTL located on chromosome 2 the reduced pyruvate conferring QTL located on chromosome 1 and the reduced pyruvate conferring QTL located on chromosome 7 as further described herein can be identified. Molecular markers which are closely linked to one of the herein described reduced pyruvate conferring QTLs, e.g. markers at a 5 cM distance or less, can then be used in detecting and/or selecting plants or plant parts comprising or retaining the reduced pungency allele (e.g. in an introgression fragment). Such closely linked molecular markers can replace phenotypic selection (or be used in addition to phenotypic selection) in breeding programs, i.e. in Marker Assisted Selection (MAS). Preferably, linked markers are used in MAS. More preferably, flanking markers are used in MAS, i.e. one marker on either side of one or more of the herein described QTLs conferring a reduced pyruvate level in an *Allium cepa* plant or plant part.

As described herein, different specific SNP markers that are linked to different reduced pyruvate conferring QTLs were identified, wherein one reduced pyruvate conferring QTLs is located on chromosome 2, one reduced pyruvate conferring QTL is located on chromosome 1 and one reduced pyruvate conferring QTL is located on chromosome 7. The method of the present invention for identifying and/or selecting an *Allium cepa* plant or plant part thus may comprise determining in said plant or plant part the presence or absence of one or more (e.g. at least 2, 3, 4 or 4) markers selected from the group consisting of: SNP_01 comprising a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 on chromosome 2; SNP_02 comprising an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3 on chromosome 2; SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5 on chromosome 2; SNP_04 comprising a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2; SNP_05 comprising a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9 on chromosome 1; SNP_06 comprising an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11 on chromosome 1; SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13 on chromosome 1; SNP_08 comprising a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15 on chromosome 1; SNP_09 comprising a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17 on chromosome 7;

SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7; SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 on chromosome 2; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23 on chromosome 2; SNP_13 comprising a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25 on chromosome 2; SNP_14 comprising an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27 on chromosome 2; SNP_15 comprising a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO: 29 on chromosome 2; SNP_16 comprising an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 on chromosome 1; SNP_17 comprising an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33 on chromosome 1; SNP_18 comprising a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35 on chromosome 1; SNP_19 comprising a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37 on chromosome 1; SNP_20 comprising a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1; SNP_21 comprising a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41 on chromosome 1; SNP_22 comprising a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 on chromosome 7; SNP_23 comprising a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45 on chromosome 7; SNP_24 comprising a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47 on chromosome 7; SNP_25 comprising a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49 on chromosome 7; isotig30225_1454 comprising a Cytosine at nucleotide 61 of SEQ ID NO: 51 or at nucleotide 61 of a sequence comprising at least 95% (more preferably at least 96%, at least 97%, at least 98% or even at least 99%) identity to SEQ ID NO: 51 on chromosome 2; isotig32865_1404 comprising a Guanine at nucleotide 61 of SEQ ID NO: 53 or at nucleotide 61 of a sequence comprising at least 95% (more preferably at least 96%, at least 97%, at least 98% or even at least 99%) identity to SEQ ID NO: 53 on chromosome 2; isotig32772_1413 comprising a Guanine at nucleotide 61 of SEQ ID NO: 55 or at nucleotide 61 of a sequence comprising at least 95% (more preferably at least 96%, at least 97%, at least 98% or even at least 99%) identity to SEQ ID NO: 55 on chromosome 1; isotig33099_885 comprising a Thymine at nucleotide 61 of SEQ ID NO: 57 or at nucleotide 61 of a sequence comprising at least 95% (more preferably at least 96%, at least 97%, at least 98% or even at least 99%) identity to SEQ ID NO: 57 on chromosome 1; isotig28625_2789 comprising a Guanine at nucleotide 61 of SEQ ID NO: 59 or at nucleotide 61 of a sequence comprising at least 95% (more preferably at least 96%, at least 97%, at least 98% or even at least 99%) identity to SEQ ID NO: 59 on chromosome 7; and isotig41937_218 comprising a Guanine at nucleotide 61 of SEQ ID NO: 61 or at nucleotide 61 of a sequence comprising at least 95% (more preferably at least 96%, at least 97%, at least 98% or even at least 99%) identity to SEQ ID NO: 61 on chromosome 7.

The method of the present invention for identifying and/or selecting an *Allium cepa* plant or plant part preferably may comprise determining in said plant or plant part the presence or absence of one or more (e.g. at least 2, 3, 4 or 4) markers selected from the group consisting of: SNP_01 comprising a Thymine at nucleotide 51 of SEQ ID NO: 1 or at nucleotide 51 of a sequence comprising at least 95% (more preferably at least 96%, at least 97%, at least 98% or even at least 99%) identity to SEQ ID NO: 1 on chromosome 2; SNP_02 comprising an Adenine at nucleotide 51 of SEQ ID NO: 3 or at nucleotide 51 of a sequence comprising at least 95% (more preferably at least 96%, at least 97%, at least 98% or even at least 99%) identity to SEQ ID NO: 3 on chromosome 2; SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5 on chromosome 2; SNP_04 comprising a Thymine at nucleotide 51 of SEQ ID NO: 7 or at nucleotide 51 of a sequence comprising at least 95% (more preferably at least 96%, at least 97%, at least 98% or even at least 99%) identity to SEQ ID NO: 7 on chromosome 2; SNP_05 comprising a Cytosine at nucleotide 51 of SEQ ID NO: 9 or at nucleotide 51 of a sequence comprising at least 95% (more preferably at least 96%, at least 97%, at least 98% or even at least 99%) identity to SEQ ID NO: 9 on chromosome 1; SNP_06 comprising an Adenine at nucleotide 51 of SEQ ID NO: 11 or at nucleotide 51 of a sequence comprising at least 95% (more preferably at least 96%, at least 97%, at least 98% or even at least 99%) identity to SEQ ID NO: 11 on chromosome 1; SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13 on chromosome 1; SNP_08 comprising a Thymine at nucleotide 51 of SEQ ID NO: 15 or at nucleotide 51 of a sequence comprising at least 95% (more preferably at least 96%, at least 97%, at least 98% or even at least 99%) identity to SEQ ID NO: 15 on chromosome 1; SNP_09 comprising a Thymine at nucleotide 51 of SEQ ID NO: 17 or at nucleotide 51 of a sequence comprising at least 95% (more preferably at least 96%, at least 97%, at least 98% or even at least 99%) identity to SEQ ID NO: 17 on chromosome 7; SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19 on chromosome 7; SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21 on chromosome 2; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23 on chromosome 2; SNP_13 comprising a Thymine at nucleotide 51 of SEQ ID NO: 25 or at nucleotide 51 of a sequence comprising at least 95% (more preferably at least 96%, at least 97%, at least 98% or even at least 99%) identity to SEQ ID NO: 25 on chromosome 2; SNP_14 comprising an Adenine at nucleotide 51 of SEQ ID NO: 27 or at nucleotide 51 of a sequence comprising at least 95% (more preferably at least 96%, at least 97%, at least 98% or even at least 99%) identity to SEQ ID NO: 27 on chromosome 2; SNP_15 comprising a Guanine at nucleotide 51 of SEQ ID NO: 29 or at nucleotide 51 of a sequence comprising at least 95% (more preferably at least 96%, at least 97%, at least 98% or even at least 99%) identity to SEQ ID NO: 29 on chromosome 2; SNP_16 comprising an Adenine at nucleotide 51 of SEQ ID NO: 31 or at nucleotide 51 of a sequence comprising at least 95% (more preferably at least 96%, at least 97%, at least 98% or even at least 99%) identity to SEQ ID NO: 31 on chromosome 1; SNP_17 comprising an Adenine at nucleotide 51 of SEQ ID NO: 33 or at nucleotide 51 of a sequence comprising at least 95% (more preferably at least 96%, at least 97%, at least 98% or even at least 99%) identity to SEQ ID NO: 33 on chromosome 1; SNP_18 comprising a Thymine at nucleotide 51 of SEQ ID NO: 35 or at nucleotide 51 of a sequence comprising at least 95% (more preferably at least 96%, at least 97%, at least 98% or even at least 99%) identity to SEQ ID NO: 35 on chromosome 1; SNP_19 comprising a Thymine at nucleotide 51 of SEQ ID NO: 37 or at nucleotide 51 of a sequence comprising at least 95% (more preferably at least 96%, at least 97%, at least 98% or even at least 99%) identity to SEQ ID NO: 37 on chromosome 1; SNP_20 comprising a Guanine at nucleotide 51 of SEQ ID NO: 39 or at nucleotide 51 of a sequence comprising at least 95% (more preferably at least 96%, at least 97%, at least 98% or even at least 99%) identity to SEQ ID NO: 39 on chromosome 1; SNP_21 comprising a Cytosine at nucleotide 51 of SEQ ID NO: 41 or at nucleotide 51 of a sequence comprising at least 95% (more preferably at least 96%, at least 97%, at least 98% or even at least 99%) identity to SEQ ID NO: 41 on chromosome 1; SNP_22 comprising a Thymine at nucleotide 51 of SEQ ID NO: 43 or at nucleotide 51 of a sequence comprising at least 95% (more preferably at least 96%, at least 97%, at least 98% or even at least 99%) identity to SEQ ID NO: 43 on chromosome 7; SNP_23 comprising a Thymine at nucleotide 51 of SEQ ID NO: 45 or at nucleotide 51 of a sequence comprising at least 95% (more preferably at least 96%, at least 97%, at least 98% or even at least 99%) identity to SEQ ID NO: 45 on chromosome 7; SNP_24 comprising a Cytosine at nucleotide 51 of SEQ ID NO: 47 or at nucleotide 51 of a sequence comprising at least 95% (more preferably at least 96%, at least 97%, at least 98% or even at least 99%) identity to SEQ ID NO: 47 on chromosome 7; SNP_25 comprising a Guanine at nucleotide 51 of SEQ ID NO: 49 or at nucleotide 51 of a sequence comprising at least 95% (more preferably at least 96%, at least 97%, at least 98% or even at least 99%) identity to SEQ ID NO: 49 on chromosome 7; isotig30225_1454 comprising a Cytosine at nucleotide 61 of SEQ ID NO: 51 or at nucleotide 61 of a sequence comprising at least 95% (more preferably at least 96%, at least 97%, at least 98% or even at least 99%) identity to SEQ ID NO: 51 on chromosome 2; isotig32865_1404 comprising a Guanine at nucleotide 61 of SEQ ID NO: 53 or at nucleotide 61 of a sequence comprising at least 95% (more preferably at least 96%, at least 97%, at least 98% or even at least 99%) identity to SEQ ID NO: 53 on chromosome 2; isotig32772_1413 comprising a Guanine at nucleotide 61 of SEQ ID NO: 55 or at nucleotide 61 of a sequence comprising at least 95% (more preferably at least 96%, at least 97%, at least 98% or even at least 99%) identity to SEQ ID NO: 55 on chromosome 1; isotig33099_885 comprising a Thymine at nucleotide 61 of SEQ ID NO: 57 or at nucleotide 61 of a sequence comprising at least 95% (more preferably at least 96%, at least 97%, at least 98% or even at least 99%) identity to SEQ ID NO: 57 on chromosome 1; isotig28625_2789 comprising a Guanine at nucleotide 61 of SEQ ID NO: 59 or at nucleotide 61 of a sequence comprising at least 95% (more preferably at least 96%, at least 97%, at least 98% or even at least 99%) identity to SEQ ID NO: 59 on chromosome 7; and isotig41937_218 comprising a Guanine at nucleotide 61 of SEQ ID NO: 61 or at nucleotide 61 of a sequence comprising at least 95% (more preferably at least 96%, at least 97%, at least 98% or even at least 99%) identity to SEQ ID NO: 61 on chromosome 7.

Preferably, the marker used in the method according to the present invention is a fragment length polymorphism (RFLP) marker, a cleaved amplified polymorphic sequence (CPAS) marker, a microsatellite marker, a restriction fragment length polymorphism (RFLP) marker, a random amplification of polymorphic DNA (RAPD) marker, an amplified fragment length polymorphism (AFLP) marker or a single nucleotide polymorphism (SNP) marker, preferably a SNP marker.

Preferably, the marker used in the method according to the present invention that is linked to a reduced pyruvate conferring QTL located on chromosome 2 is a SNP marker selected from the group consisting of: SNP_11 comprising an Adenine at nucleotide 51 of SEQ ID NO: 21 or at nucleotide 51 of a sequence comprising at least 95% (more preferably at least 96%, at least 97%, at least 98% or even at least 99%) identity to SEQ ID NO: 21; SNP_12 comprising a Cytosine at nucleotide 51 of SEQ ID NO: 23 or at nucleotide 51 of a sequence comprising at least 95% (more preferably at least 96%, at least 97%, at least 98% or even at least 99%) identity to SEQ ID NO: 23; SNP_13 comprising a Thymine at nucleotide 51 of SEQ ID NO: 25 or at nucleotide 51 of a sequence comprising at least wherein 95% (more preferably at least 96%, at least 97%, at least 98% or even at least 99%) identity to SEQ ID NO: 25; SNP_14 comprising an Adenine at nucleotide 51 of SEQ ID NO: 27 or at nucleotide 51 of a sequence comprising at least wherein 95% (more preferably at least 96%, at least 97%, at least 98% or even at least 99%) identity to SEQ ID NO: 27; SNP_01 comprising a Thymine at nucleotide 51 of SEQ ID NO: 1 or at nucleotide 51 of a sequence comprising at least wherein 95% (more preferably at least 96%, at least 97%, at least 98% or even at least 99%) identity to SEQ ID NO: 01;

SNP_02 comprising an Adenine at nucleotide 51 of SEQ ID NO: 3 or at nucleotide 51 of a sequence comprising at least wherein 95% (more preferably at least 96%, at least 97%, at least 98% or even at least 99%) identity to SEQ ID NO: 3; SNP_03 comprising a Cytosine at nucleotide 51 of SEQ ID NO: 5 or at nucleotide 51 of a sequence comprising at least wherein 95% (more preferably at least 96%, at least 97%, at least 98% or even at least 99%) identity to SEQ ID NO: 5; SNP_04 comprising a Thymine at nucleotide 51 of SEQ ID NO: 7 or at nucleotide 51 of a sequence comprising at least wherein 95% (more preferably at least 96%, at least 97%, at least 98% or even at least 99%) identity to SEQ ID NO: 7; SNP_15 comprising a Guanine at nucleotide 51 of SEQ ID NO: 29 or at nucleotide 51 of a sequence comprising at least wherein 95% (more preferably at least 96%, at least 97%, at least 98% or even at least 99%) identity to SEQ ID NO: 29; isotig30225_1454 comprising a Cytosine at nucleotide 61 of SEQ ID NO: 51 or at nucleotide 61 of a sequence comprising at least 95% (more preferably at least 96%, at least 97%, at least 98% or even at least 99%) identity to SEQ ID NO: 51; and isotig32865_1404 comprising a Guanine at nucleotide 61 of SEQ ID NO: 53 or at nucleotide 61 of a sequence comprising at least 95% (more preferably at least 96%, at least 97%, at least 98% or even at least 99%) identity to SEQ ID NO: 53.

Preferably, the marker used in the method according to the present invention that is linked to a reduced pyruvate conferring QTL located on chromosome 1 is s a SNP marker elected from the group consisting of: SNP_16 comprising an Adenine at nucleotide 51 of SEQ ID NO: 31 or at nucleotide 51 of a sequence comprising at least wherein 95% (more preferably at least 96%, at least 97%, at least 98% or even at least 99%) identity to SEQ ID NO: 31; SNP_17 comprising an Adenine at nucleotide 51 of SEQ ID NO: 33 or at nucleotide 51 of a sequence comprising at least wherein 95% (more preferably at least 96%, at least 97%, at least 98% or even at least 99%) identity to SEQ ID NO: 33; SNP_05 comprising a Cytosine at nucleotide 51 of SEQ ID NO: 9 or at nucleotide 51 of a sequence comprising at least wherein 95% (more preferably at least 96%, at least 97%, at least 98% or even at least 99%) identity to SEQ ID NO: 9; SNP_06 comprising an Adenine at nucleotide 51 of SEQ ID NO: 11 or at nucleotide 51 of a sequence comprising at least wherein 95% (more preferably at least 96%, at least 97%, at least 98% or even at least 99%) identity to SEQ ID NO: 11; SNP_07 comprising a Cytosine at nucleotide 51 of SEQ ID NO: 13 or at nucleotide 51 of a sequence comprising at least wherein 95% (more preferably at least 96%, at least 97%, at least 98% or even at least 99%) identity to SEQ ID NO: 13; SNP_08 comprising a Thymine at nucleotide 51 of SEQ ID NO: 15 or at nucleotide 51 of a sequence comprising at least wherein 95% (more preferably at least 96%, at least 97%, at least 98% or even at least 99%) identity to SEQ ID NO: 15; SNP_18 comprising a Thymine at nucleotide 51 of SEQ ID NO: 35 or at nucleotide 51 of a sequence comprising at least wherein 95% (more preferably at least 96%, at least 97%, at least 98% or even at least 99%) identity to SEQ ID NO: 35; SNP_19 comprising a Thymine at nucleotide 51 of SEQ ID NO: 37 or at nucleotide 51 of a sequence comprising at least wherein 95% (more preferably at least 96%, at least 97%, at least 98% or even at least 99%) identity to SEQ ID NO: 37; SNP_20 comprising a Guanine at nucleotide 51 of SEQ ID NO: 39 or at nucleotide 51 of a sequence comprising at least wherein 95% (more preferably at least 96%, at least 97%, at least 98% or even at least 99%) identity to SEQ ID NO: 39; SNP_21 comprising a Cytosine at nucleotide 51 of SEQ ID NO: 41 or at nucleotide 51 of a sequence comprising at least wherein 95% (more preferably at least 96%, at least 97%, at least 98% or even at least 99%) identity to SEQ ID NO: 41; isotig32772_1413 comprising a Guanine at nucleotide 61 of SEQ ID NO: 55 or at nucleotide 61 of a sequence comprising at least 95% (more preferably at least 96%, at least 97%, at least 98% or even at least 99%) identity to SEQ ID NO: 55; and isotig33099_885 comprising a Thymine at nucleotide 61 of SEQ ID NO: 57 or at nucleotide 61 of a sequence comprising at least 95% (more preferably at least 96%, at least 97%, at least 98% or even at least 99%) identity to SEQ ID NO: 57.

Preferably, the marker used in the method according to the present invention that is linked to a reduced pyruvate conferring QTL located on chromosome 7 is a SNP marker selected from the group consisting of: SNP_22 comprising a Thymine at nucleotide 51 of SEQ ID NO: 43 or at nucleotide 51 of a sequence comprising at least wherein 95% (more preferably at least 96%, at least 97%, at least 98% or even at least 99%) identity to SEQ ID NO: 43; SNP_23 comprising a Thymine at nucleotide 51 of SEQ ID NO: 45 or at nucleotide 51 of a sequence comprising at least wherein 95% (more preferably at least 96%, at least 97%, at least 98% or even at least 99%) identity to SEQ ID NO: 45; SNP_24 comprising a Cytosine at nucleotide 51 of SEQ ID NO: 47 or at nucleotide 51 of a sequence comprising at least wherein 95% (more preferably at least 96%, at least 97%, at least 98% or even at least 99%) identity to SEQ ID NO: 47; SNP_25 comprising a Guanine at nucleotide 51 of SEQ ID NO: 49 or at nucleotide 51 of a sequence comprising at least wherein 95% (more preferably at least 96%, at least 97%, at least 98% or even at least 99%) identity to SEQ ID NO: 49; SNP_09 comprising a Thymine at nucleotide 51 of SEQ ID NO: 17 or at nucleotide 51 of a sequence comprising at least wherein 95% (more preferably at least 96%, at least 97%, at least 98% or even at least 99%) identity to SEQ ID NO: 17; and SNP_10 comprising a Guanine at nucleotide 51 of SEQ ID NO: 19 or at nucleotide 51 of a sequence comprising at least wherein 95% (more preferably at least 96%, at least 97%, at least 98% or even at least 99%) identity to SEQ ID NO: 19; isotig28625_2789 comprising a Guanine at nucleotide 61 of SEQ ID NO: 59 or at nucleotide 61 of a sequence comprising at least 95% (more preferably at least 96%, at least 97%, at least 98% or even at least 99%) identity to SEQ ID NO: 59; and isotig41937_218 comprising a Guanine at nucleotide 61 of SEQ ID NO: 61 or at nucleotide 61 of a sequence comprising at least 95% (more preferably at least 96%, at least 97%, at least 98% or even at least 99%) identity to SEQ ID NO: 61.

Preferably, the method according to the present invention for identifying and/or selecting an *Allium cepa* plant or plant part comprises determining in said plant or plant part the presence or absence of more than one marker. Accordingly, the method according to the present invention for identifying and/or selecting an *Allium cepa* plant or plant part may comprise determining in said plant or plant part the presence or absence of at least one (e.g. at least 2, 3, 4 or 4) marker(s) linked to a reduced pyruvate conferring QTL located on chromosome 2 and at least one (e.g. at least 2, 3, 4 or 4) marker(s) linked to a reduced pyruvate conferring QTL located on chromosome 1. The method according to the present invention for identifying and/or selecting an *Allium cepa* plant or plant part may also comprise determining in said plant or plant part the presence or absence of at least one (e.g. at least 2, 3, 4 or 4) marker(s) linked to a reduced pyruvate conferring QTL located on chromosome 2 and at least one (e.g. at least 2, 3, 4 or 4) marker(s) linked to a reduced pyruvate conferring QTL located on chromosome 7.

The method according to the present invention for identifying and/or selecting an *Allium cepa* plant or plant part may also comprise determining in said plant or plant part the presence or absence of at least one (e.g. at least 2, 3, 4 or 4) marker(s) linked to a reduced pyruvate conferring QTL located on chromosome 1 and at least one (e.g. at least 2, 3, 4 or 4) marker(s) linked to a reduced pyruvate conferring QTL located on chromosome 7. Even more preferably, the method according to the present invention for identifying and/or selecting an *Allium cepa* plant or plant part comprises determining in said plant or plant part the presence or absence of at least one (e.g. at least 2, 3, 4 or 4) marker(s) linked to a reduced pyruvate conferring QTL located on chromosome 2, at least one (e.g. at least 2, 3, 4 or 4) marker(s) linked to a reduced pyruvate conferring QTL located on chromosome 1 and at least one (e.g. at least 2, 3, 4 or 4) marker(s) linked to a reduced pyruvate conferring QTL located on chromosome 7.

Preferably, the method according to the present invention for identifying and/or selecting an *Allium cepa* plant or plant part comprises determining in said plant or plant part the presence or absence of at least one marker linked to a reduced pyruvate conferring QTL located on chromosome 2, at least one marker linked to a reduced pyruvate conferring QTL located on chromosome 1 and at least one marker linked to a reduced pyruvate conferring QTL located on chromosome 7.

Preferably, the method according to the present invention for identifying and/or selecting an *Allium cepa* plant or plant part comprises determining in said plant or plant part the presence or absence of one or more (e.g. 2 or 3) peak marker, preferably one or more (e.g. 2 or 3) of the peak markers as described in Table 2. As used herein, the term "peak marker" describes a marker that is found to be as accurate as possible, preferably with a false-positive and/or false-negative rate of 0%.

Accordingly, the marker linked to a reduced pyruvate conferring QTL located on chromosome 2 preferably is SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5. The marker linked to a reduced pyruvate conferring QTL located on chromosome 1 preferably is SNP_07 comprising a Cytosine at nucleotide 51 of SEQ ID NO: 13 or at nucleotide 51 of a sequence comprising at least 95% (more preferably at least 96%, at least 97%, at least 98% or even at least 99%) identity to SEQ ID NO: 13. The marker linked to a reduced pyruvate conferring QTL located on chromosome 7 preferably is SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

The method according to the present invention for identifying and/or selecting an *Allium cepa* plant or plant part accordingly preferably comprises determining in said plant or plant part the presence or absence of: at least one (e.g. at least 2, 3, 4 or 4) marker(s) linked to a reduced pyruvate conferring QTL located on chromosome 2, wherein the marker on chromosome 2 is SNP_03 comprising a Cytosine at nucleotide 51 of SEQ ID NO: 5 or at nucleotide 51 of a sequence comprising at least 95% (more preferably at least 96%, at least 97%, at least 98% or even at least 99%) identity to SEQ ID NO: 5; at least one (e.g. at least 2, 3, 4 or 4) marker(s) linked to a reduced pyruvate conferring QTL located on chromosome 1, wherein the marker on chromosome 1 is SNP_07 comprising a Cytosine at nucleotide 51 of SEQ ID NO: 14 or at nucleotide 51 of a sequence comprising at least 95% (more preferably at least 96%, at least 97%, at least 98% or even at least 99%) identity to SEQ ID NO: 14; and at least one (e.g. at least 2, 3, 4 or 4) marker(s) linked to a reduced pyruvate conferring QTL located on chromosome 7, wherein the marker on chromosome 7 is SNP_10 comprising a Guanine at nucleotide 51 of SEQ ID NO: 19 or at nucleotide 51 of a sequence comprising at least 95% (more preferably at least 96%, at least 97%, at least 98% or even at least 99%) identity to SEQ ID NO: 19.

Nucleic Acids and Use Thereof

The present invention further provides an isolated nucleic acid comprising the nucleotide sequence selected from the group consisting of: SEQ ID NO: 1 or a fragment thereof consisting of at least 15 nucleotides comprising nucleotide 51 of SEQ ID NO: 1; SEQ ID NO: 3 or a fragment thereof consisting of at least 15 nucleotides comprising nucleotide 51 of SEQ ID NO: 3; SEQ ID NO: 5 or a fragment thereof consisting of at least 15 nucleotides comprising nucleotide 51 of SEQ ID NO: 5; SEQ ID NO: 7 or a fragment thereof consisting of at least 15 nucleotides comprising nucleotide 51 of SEQ ID NO: 7; SEQ ID NO: 9 or a fragment thereof consisting of at least 15 nucleotides comprising nucleotide 51 of SEQ ID NO: 9; SEQ ID NO: 11 or a fragment thereof consisting of at least 15 nucleotides comprising nucleotide 51 of SEQ ID NO: 11; SEQ ID NO: 13 or a fragment thereof consisting of at least 15 nucleotides comprising nucleotide 51 of SEQ ID NO: 13; SEQ ID NO: 15 or a fragment thereof consisting of at least 15 nucleotides comprising nucleotide 51 of SEQ ID NO: 15; SEQ ID NO: 17 or a fragment thereof consisting of at least 15 nucleotides comprising nucleotide 51 of SEQ ID NO: 17; SEQ ID NO: 19 or a fragment thereof consisting of at least 15 nucleotides comprising nucleotide 51 of SEQ ID NO: 19, SEQ ID NO: 21 or a fragment thereof consisting of at least 15 nucleotides comprising nucleotide 51 of SEQ ID NO: 21; SEQ ID NO: 23 or a fragment thereof consisting of at least 15 nucleotides comprising nucleotide 51 of SEQ ID NO: 23; SEQ ID NO: 25 or a fragment thereof consisting of at least 15 nucleotides comprising nucleotide 51 of SEQ ID NO: 25; SEQ ID NO: 27 or a fragment thereof consisting of at least 15 nucleotides comprising nucleotide 51 of SEQ ID NO: 27; SEQ ID NO: 29 or a fragment thereof consisting of at least 15 nucleotides comprising nucleotide 51 of SEQ ID NO: 29; SEQ ID NO: 31 or a fragment thereof consisting of at least 15 nucleotides comprising nucleotide 51 of SEQ ID NO: 31; SEQ ID NO: 33 or a fragment thereof consisting of at least 15 nucleotides comprising nucleotide 51 of SEQ ID NO: 33; SEQ ID NO: 35 or a fragment thereof consisting of at least 15 nucleotides comprising nucleotide 51 of SEQ ID NO: 35; SEQ ID NO: 37 or a fragment thereof consisting of at least 15 nucleotides comprising nucleotide 51 of SEQ ID NO: 37; SEQ ID NO: 39 or a fragment thereof consisting of at least 15 nucleotides comprising nucleotide 51 of SEQ ID NO: 39; SEQ ID NO: 41 or a fragment thereof consisting of at least 15 nucleotides comprising nucleotide 51 of SEQ ID NO: 41; SEQ ID NO: 43 or a fragment thereof consisting of at least 15 nucleotides comprising nucleotide 51 of SEQ ID NO: 43; SEQ ID NO: 45 or a fragment thereof consisting of at least 15 nucleotides comprising nucleotide 51 of SEQ ID NO: 45; SEQ ID NO: 47 or a fragment thereof consisting of at least 15 nucleotides comprising nucleotide 51 of SEQ ID NO: 47; and SEQ ID NO: 49 or a fragment thereof consisting of at least 15 nucleotides comprising nucleotide 51 of SEQ ID NO: 49, or comprising the complementary nucleotide sequence thereof. The present invention preferably provides an isolated nucleic acid comprising the nucleotide sequence selected from the group consisting of: SEQ ID NO: 1 or a fragment thereof consisting of at least 15 nucleotides comprising nucleotide 51 of SEQ ID NO: 1; SEQ ID NO: 3 or a fragment thereof consisting of at least 15 nucleotides comprising nucleotide 51 of SEQ ID NO: 3; SEQ ID NO: 5 or a fragment thereof consisting of at least 15 nucleotides comprising nucleotide 51 of SEQ ID NO: 5; SEQ ID NO: 7 or a fragment thereof consisting of at least 15 nucleotides comprising nucleotide 51 of SEQ ID NO: 7; SEQ ID NO: 9 or a fragment thereof consisting of at least 15 nucleotides comprising nucleotide 51 of SEQ ID NO: 9; SEQ ID NO: 11 or a fragment thereof consisting of at least 15 nucleotides comprising nucleotide 51 of SEQ ID NO: 11; SEQ ID NO: 13 or a fragment thereof consisting of at least 15 nucleotides comprising nucleotide 51 of SEQ ID NO: 13; SEQ ID NO: 15 or a fragment thereof consisting of at least 15 nucleotides comprising nucleotide 51 of SEQ ID NO: 15; SEQ ID NO: 17 or a fragment thereof consisting of at least 15 nucleotides comprising nucleotide 51 of SEQ ID NO: 17; SEQ ID NO: 19 or a fragment thereof consisting of at least 15 nucleotides comprising nucleotide 51 of SEQ ID NO: 19, SEQ ID NO: 21 or a fragment thereof consisting of at least 15 nucleotides comprising nucleotide 51 of SEQ ID NO: 21; SEQ ID NO: 23 or a fragment thereof consisting of at least 15 nucleotides comprising nucleotide 51 of SEQ ID NO: 23; SEQ ID NO: 25 or a fragment thereof consisting of at least 15 nucleotides comprising nucleotide 51 of SEQ ID NO: 25; SEQ ID NO: 27 or a fragment thereof consisting of at least 15 nucleotides comprising nucleotide 51 of SEQ ID NO: 27; SEQ ID NO: 31 or a fragment thereof consisting of at least 15 nucleotides comprising nucleotide 51 of SEQ ID NO: 31; SEQ ID NO: 33 or a fragment thereof consisting of at least 15 nucleotides comprising nucleotide 51 of SEQ ID NO: 33; SEQ ID NO: 35 or a fragment thereof consisting of at least 15 nucleotides comprising nucleotide 51 of SEQ ID NO: 35; SEQ ID NO: 37 or a fragment thereof consisting of at least 15 nucleotides comprising nucleotide 51 of SEQ ID NO: 37; SEQ ID NO: 39 or a fragment thereof consisting of at least 15 nucleotides comprising nucleotide 51 of SEQ ID NO: 39; SEQ ID NO: 43 or a fragment thereof consisting of at least 15 nucleotides comprising nucleotide 51 of SEQ ID NO: 43; SEQ ID NO: 45 or a fragment thereof consisting of at least 15 nucleotides comprising nucleotide 51 of SEQ ID NO: 45; SEQ ID NO: 47 or a fragment thereof consisting of at least 15 nucleotides comprising nucleotide 51 of SEQ ID NO: 47; and SEQ ID NO: 49 or a fragment thereof consisting of at least 15 nucleotides comprising nucleotide 51 of SEQ ID NO: 49, or comprising the complementary nucleotide sequence thereof.

Accordingly, the isolated nucleic acid as provided herein comprises at least 15 nucleotides comprising nucleotide 51 of any one of the nucleotide sequences selected from the group consisting of SEQ ID NOs: 1-50. Furthermore, the isolated nucleic acid as provided herein comprises the complementary sequence of the isolated nucleic acid comprising at least 15 nucleotides comprising nucleotide 51 of any one of the nucleotide sequences selected from the group consisting of SEQ ID NOs: 1-50. This means that the isolated nucleic acid as provided herein comprises a fragment of any one of the nucleotide sequences selected from the group consisting of SEQ ID NOs: 1-50 of at least 15 subsequent nucleotides wherein said fragment further comprises nucleotide 51 of said nucleotide sequences selected from the group consisting of SEQ ID NOs: 1-50 or complementary nucleotide sequences thereof. Preferably, the isolated nucleic acid of the present invention comprises more than 15 nucleotides comprising nucleotide 51 of any one of the nucleotide sequences selected from the group consisting of SEQ ID NOs: 1-50, for instance at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 nucleotides comprising nucleotide 51 of any one of the nucleotide sequences selected from the group consisting of SEQ ID NOs: 1-50, or the complementary nucleotide sequence thereof.

The nucleic acid according to the present invention is particularly useful for use in or the development of the method for identifying and/or selecting an *Allium cepa* plant or plant part, but also for a method of producing an *Allium cepa* plant comprising crossing a first *Allium cepa* plant with a second *Allium cepa* plant and selecting from the offspring of said crossing an *Allium cepa* plant based on the presence or absence of one or more markers of the present invention. Accordingly, the present invention provides for the use of one or more of the nucleotide sequences selected from the group consisting of consisting of SEQ ID NOs: 1-50, preferably consisting of SEQ ID NOs: 1-50, or a fragment thereof for marker assisted selection of an *Allium cepa* plant or plant part, wherein said fragment consists of at least 15 nucleotides comprising nucleotide 51 of said nucleotide sequences selected from the group consisting of SEQ ID NOs: 1-50 or a complementary sequence of said one or more of the nucleotide sequences. Furthermore, the present invention provides for the use of one or more of the nucleotide sequences selected from the group consisting of consisting of SEQ ID NOs: 51-62, preferably consisting of SEQ ID NOs: 51-62, or a fragment thereof for marker assisted selection of an *Allium cepa* plant or plant part, wherein said fragment consists of at least 15 nucleotides comprising nucleotide 61 of said nucleotide sequences selected from the group consisting of SEQ ID NOs: 51-62 or a complementary sequence of said one or more of the nucleotide sequences. Preferably, the nucleotide sequences used in accordance with the present invention may be any one of the nucleotide sequences as described herein, e.g. comprising more than 15 nucleotides comprising nucleotide 51 of any one of the nucleotide sequences selected from the group consisting of SEQ ID NOs: 1-50, respectively comprising more than 15 nucleotides comprising nucleotide 61 of any one of the nucleotide sequences selected from the group consisting of SEQ ID NOs: 51-62, for instance at least 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 nucleotides comprising nucleotide 51 of any one of the nucleotide sequences selected from the group consisting of SEQ ID NOs: 1-50, respectively comprising nucleotide 61 of any one of the nucleotide sequences selected from the group consisting of SEQ ID NOs: 51-62, or a complementary sequence of said nucleotide sequences.

Seed Deposits

Representative samples of seeds comprising the QTLs conferring a reduced pyruvate level as described herein were deposited by Nunhems B.V. on Mar. 13, 2008 at the American Type Culture Collection (ATCC, 10801 University Boulevard, Manassas, VA 20110-2209, USA) according to the Budapest Treaty, under the Expert Solution (EPC 2000, Rule 32(1)). Seeds were given the following deposit numbers PTA-9053 (seeds of line I37853B as further described in WO 2009/092560 A1), PTA-9054 (seeds of line I37554A as further described in WO 2009/092560 A1) and PTA-9055 (seeds of line I37554B as further described in WO 2009/092560 A1).

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer and will be replaced if it ever becomes nonviable during that period. Applicant does not waive any rights granted under this patent on this application or under the Plant Variety Protection Act (7 USC 2321 et seq.).

EXAMPLES

Example 1

QTL Mapping

A single low pungency (reduced pungency) line I37720B, derived from a cross between I37554B and material in the pedigree of I37554B, was crossed with two pungent inbred lines I37977B ("population 1") and I37545-7 ("population 2"). The resulting F1 hybrids were self-pollinated to produce two segregating populations of F2 plants. In population 1, a total of 331 F2 plants were grown, and in population 2, a total of 236 plants were grown under field conditions in Brooks, OR. Leaf tissue was collected from each F2 individual for DNA extraction. Bulbs were harvested and stored for four months, after which the pyruvate level was measured.

A panel of 283 KASP markers was run on the DNA extracted from each F2 individual. Monomorphic markers were discarded, and a genetic linkage map was calculated for each population independently using using Kosambi's mapping function in the JoinMap software package. The resulting maps were used in combination with the pyruvate measurements to identify quantitative trait loci (QTL) using the interval mapping method in the MapQTL software package. The logarithm of the odds (LOD) score threshold for significant association of loci with pyruvate concentration was set using the genome wide permutation testing method with a cumulative count of at least 0.95, with 200 iterations of 1,000 permutations for each population.

In population 1 there were two significant QTL detected which exceeded the calculated LOD threshold, one on linkage group 3 (chromosome 2) and one on linkage group 6 (chromosome 7). Population 2 contained a single significant QTL on linkage group 4 (chromosome 1). Peak markers for the three QTL were identified on an integrated genetic linkage map and additional nearby markers were added to the F2 population map. The number of additional markers added is detailed in Table 1. Information on the peak and flanking markers for each significant QTL is in Table 2.

After integrating additional markers, the peak marker for the QTL on linkage group 3 (chromosome 2) explained 5.6% of the variation in pyruvic acid values, the peak marker for the QTL on linkage group 4 (chromosome 1) explained 45.6% of the variation, and the peak marker for the QTL on linkage group 6 (chromosome 7) explained 6.5% of the variation in pyruvic acid values.

TABLE 1

| QTL | Additional markers | Monomorphic | Polymorphic | In QTL interval |
|---|---|---|---|---|
| Linkage group 3 | 19 | 8 | 11 | 1 |
| Linkage group 4 | 5 | 4 | 1 | 1 |
| Linkage group 6 | 12 | 5 | 7 | 4 |

Additional markers added at each of the three significant QTL

TABLE 2

Names of peak and flanking markers
for each of the significant QTL

| QTL | Flanking | Peak | Flanking |
|---|---|---|---|
| Linkage group 3 | SNP__11 | SNP__03 | SNP__04 |
| Linkage group 4 | SNP__16 | SNP__07 | SNP__20 |
| Linkage group 6 | SNP__22 | SNP__10 | SNP__10* |

*SNP__10 is the most distal marker on linkage group 6, so there is no true flanking marker

TABLE 3

Nucleotide sequences of the
identified peak and flanking markers

SNP__01    CATGGCAAGAAAAATGTTCCAAGCTTCTTGAAACATCTCCAGACAATTGG[T/G]
CTTTCAAAAGTGATTCCGAAACCTCTACTTCGAAGTACATTGCTTCTTTA
(SEQ ID NO: 1)

SNP__02    TTGATAAAAGCGATATTGTTGGGGAAGTATCCTGCAGAATTTTTGTGGCC[G/A]
TGAAAAGGAAGATGAGTGGAAGCTAAATGCATTGGAAATTGTGTTTGGCC
(SEQ ID NO: 3)

SNP__03    GACGGATAATTCAGAACAGGGAGGAAGTAAGCAGCATGTGATAATCAACA[T/C]
AGAGGATAGAGCTTCTGAGGTGGGTAAAGCTGATGCGAATCGTCCCACGC
(SEQ ID NO: 5)

SNP__04    TGATGCTATCTGGAAGATTACAAATTTATAGATGGTATGGGATGTTGGAA[T/C]
AGCAGATTGGTGCTGAATTTAGTACTACCAAAGGACAGATGACGCCGCTT
(SEQ ID NO: 7)

SNP__05    CTCAGGAATGAGATTTGCATCAGCATCCTCAGGATCAATTTCTTGATCAT[T/C]
AGATTGCATTCCATAATTAAACAGCAGCTCGTGCCACTTCATGTCATCAA
(SEQ ID NO: 9)

SNP__06    CCTGAGCGATGTAAAAGGAAGAGATAGAGTATGGGAGTTGAGAAACTGTA[A/G]
CCATGTTTTTCATAAAGGATGCCTGGACAAATGGTTAGAGCATGATGAGC
(SEQ ID NO: 11)

SNP__07    GATTGTTTAGACATTCGTTGTATTTCGCGAGATCTGCTCACGGGATAGCT[G/C]
ATTTTTTAAGATTTTTCGAGAAATTCTACCTGGATTTTTGTTAGGGTTTT
(SEQ ID NO: 13)

SNP__08    AATTACACTTTAGCAATCAAGAGATGATTCTCAGGAGAAATATCCGAGGA[T/G]
GTATACTTCACCATTTGTGCATCCAACCCCTGATCCCTTAGCCACGACAT
(SEQ ID NO: 15)

SNP__09    GATGATGGTGGAGCGAGAAGAGAATGGTTCTGGTTTGTGGTTTGATTGGA[T/C]
GGGTTTGTCGATCGAGGTCCATGACCATTGCTTGTGGATGCGGTTCCATC
(SEQ ID NO: 17)

SNP__10    GAGCAAGATCAGTTAAGATTCTTAAAGCTCTTTGAAGACACCGATGAGTT[G/C]
GATGATGAGTTGGAACAATTATAAGTTCAATCTACTACGCCATACTTTAC
(SEQ ID NO: 19)

SNP__11    ACTTATTTGTACCAGATGCTAGTTCATCATACGATCTCGATCAACAGCTC[A/G]
AAACTGTCCCCACTTCATCTGACGGCAATATCATGGTTTCTTGGAATCCT
(SEQ ID NO: 21)

SNP__12    ACTCTTTTCAAAATGGCAATTCCAAAACTTGAACTTTAACTTTTGTTACA[C/T]
GCTTAATCACGTCGATAATCATGCTTAGCACCACTGCCACTTTCTAAATC
(SEQ ID NO: 23)

SNP__13    CCTGAACATTATGCAAAATGTTTAGCCACACTTTCACGCTCATCTTCACT[T/A]
GGAATTCGATTGTGTTTTCGTCAGTACAGTAAAAATAAATTCAAGCTTTT
(SEQ ID NO: 25)

SNP__14    CGTGAAAGTGTGGCTAAACATTTTGCATAATGTTCAGGAGTTAAAACCAC[A/G]
GCAATGTCATCTATACATTCTGCGCTGATCACTTGTGAGAAGGGCGTGAA
(SEQ ID NO: 27)

SNP__15    TAAGCTTCATGAAGCTATATATATCACAGTAAAACAGGTTATTTTTATGG[G/A]
CATGGATTACTTTTTAAATTTGTAAGTTGGTTTTGTCTCCCTTTTGGTTA
(SEQ ID NO: 29)

TABLE 3-continued

Nucleotide sequences of the
identified peak and flanking markers

SNP_16  ACGTCGGCGGGAGCTTTCTCGGTTTGATACACGCCTAAATAGCCGGTTGG[A/G]
       TCGACTCTCGCGTAGATCGGACCGTTGCCTTGGATTATTTGAGTTTTGGC
       (SEQ ID NO: 31)

SNP_17  TATAGTGTGGCAAAAGGTGCATTGCATAGAGCATTTGATGAGATAGTAGT[T/A]
       GTTGAAAGAAATTGTGGTCGAGAAGAGCAGAGAGATCCAATCAATATTAA
       (SEQ ID NO: 33)

SNP_18  TATTATAATTATAAGCAGTGATGTCACATTCATTAATTTGTGCACCCTCA[A/T]
       TATTATCCCTCGATGAAAAGTCAATTATTTCGTTAGGAATATCCGTAGAC
       (SEQ ID NO: 35)

SNP_19  TGTTGCATTCCCCATTACCCAATATCACTGTCACAACTATGCTCCCCAAC[A/T]
       CCTTGCTACACTGCAATAACATCACATACAACTTCACTTCCCCGAACAAC
       (SEQ ID NO: 37)

SNP_20  CTTCCCCTCGGTAAATATTCTGTTACTATCGACAAATGTGGAGACTTTGT[G/A]
       ACTGCACCCATAAATAGTACAATATTTGGATGGCGAATACGTTTCATTAT
       (SEQ ID NO: 39)

SNP_21  TACTGCCCAGTCACTGCTTGTGGGGATGGATTCTTCGTCTTCAAGCGATG[C/T]
       TCGAATTCTCTCAAGATCTTTCTCTGAAGCTTCTTTGAAATTAATGTCCT
       (SEQ ID NO: 41)

SNP_22  GATACCCAAAACCCTGATATGATCGACTATCTCAACCAAGAAAATGATTA[C/T]
       ACTGAATCATTTATGAAAGATACTGAAAAATTGCAGCGAAAATTAGTGGA
       (SEQ ID NO: 43)

SNP_23  TTATGGTCGAAAGAAGACCTATTGAACTTTGTCATAGCACCTCCAGTGGG[T/C]
       ATCTTCCCACACAGCTTATTATAGCCGACGTCAAAATACACCAGTTTGAT
       (SEQ ID NO: 45)

SNP_24  AAATTGGCTATGGAGAAGATGAAGATTGATTTGGCACAGAAAGATAAGAT[C/G]
       CTGTCTGCATTGCTGAGAAAATCAAAGGCTGATAATGAAGAAAAGCATAT
       (SEQ ID NO: 47)

SNP_25  CATTCTGTCATGGTTATCAGTCACATCTAATGATGCTTTAATACTTTCCG[G/A]
       ATTCAGAAATGACAAATGTGCTCCACCAAATGCTTCTACACATGGTTTAC
       (SEQ ID NO: 49)

Furthermore, the QTLs of the present invention were placed on publicly available genetic maps of onion. All of the public markers referenced here are detailed in Duangjit et al. (2013) Theor Appl Genet 126, 2093-2101. The "B9885×B8667" map referenced is detailed in Munaiz and Havey (2020) J. Amer. Soc. Hort. Sci., 145(1), 67-72 and the "Char×B5351" map referenced is detailed in Havey (2000) J. Amer. Soc. Hort. Sci., 145(2), 110-119. The QTLs of the present invention were located on these public maps by integrating public marker information with internal datasets, and the low pungency line I37720B was genotyped with the public markers to determine the allele linked to the reduced pyruvate locus. The publicly available markers further defining the locus of the QTLs of the present invention are described in Table 4 as provided herein below.

TABLE 4

Locus of reduced pyruvate QTLs as defined by publicly available genetic markers

| Marker | Map | Chromosome | Mapping position | Reduced pyruvate allele |
|---|---|---|---|---|
| isotig30225_1454 | B9885 × B8667 | 2 | 96.7 | C |
| isotig32865_1404 | B9885 × B8667 | 2 | 116.1 | G |
| isotig32772_1413 | Char × B5351 | 1 | 60.7 | G |
| isotig33099_885 | Char × B5351 | 1 | 75.2 | T |
| isotig28625_2789 | B9885 × B8667 | 7 | 0 | G |
| isotig41937_218 | B9885 × B8667 | 7 | 11.2 | G |

TABLE 5

Nucleotide sequences of
the publicly available genetic markers isotig30225_1454  CTCGCTTTTGTCTCCGGTCAAATACTTGAACC-
                CATC
                ATACAAAATTCTTTCAAAAACGTC[C/A]
                ACTTTTA
                TTTTTCCAAC-
                CAACACCCTTTCAGTACTCTTCTCCA
                AAACAGATAGGAACAAC (SEQ ID NO: 51)

isotig32865_1404  NAATCGAGCGGAGTTCGTCGGAGTCCAT-
                TACCGTCT
                CTTTCTTTGGCTATTTAATATCGT[G/T]
                TAATGGA TABLE 5-continued Nucleotide sequences of
the publicly available genetic markers

GGATAAAAGAGGATAATGATGTAATATTTTATG-
GAT
TGGACTATATAAAAATG (SEQ ID NO: 53)

isotig32772_1413 GAATCGCGAACCTTTGAAATGGAGGG-
GAACACCGGT
ATTGGAGCCGATACCCTTCTCGCC[G/A]GTA-
CAAA
TCGCTCTAAAATTCTCTGCCGTTCTGG-
GAACGACGT
CGGCAAAGAGCTCAATG (SEQ ID NO: 55)

isotig33099_885 AGTGCTCACTGTATTATCAATTCCG-
GAAGGTTTTCCA
TGGATAATCTNTTCACCCTCATA[C/T]GCCCAT-
TTG
TTTATGGATCAAGTTCCTTTTCCCCTAAATT-
CAACC
ACCCAGATTCTTTA (SEQ ID NO: 57)

isotig28625_2789 AGTTAAAAGCACTTCCACGCCTAGGCCACTATA-
CATA
TAGTCCTTCTCCTTCCCGTTCAC[A/G]
TACTCCTTG
CGCCTGTAAAAAGGAAGCACATCCAGCACATCTT-
CAT
TTTCCTTCAGCCAC (SEQ ID NO: 59)

isotig41937_218 NTTAAAGAGGCCTAGCGCGAGTAGTTGGATCTT-
CATT
GGATTCTACTTTCATCATGAAAA[G/T]ATACC-
CAAT
TATCCACAAGAGCACATATGGAAAAGGAATCCAG-
CAT
AAACATGCCAATAG (SEQ ID NO: 61)

Accordingly, it can be concluded that the reduced pyruvate conferring QTL located on chromosome 2 is located between public marker isotig30225_1454 (SEQ ID NO: 51) and public marker isotig32865_1404 (SEQ ID NO: 53) which represents an interval of 19.4 cM. The reduced pyruvate conferring QTL located on chromosome 1 is located between public marker isotig32772_1413 (SEQ ID NO: 55) and public marker isotig33099_885 (SEQ ID NO: 57) which represents an interval of 14.5 cM. The reduced pyruvate conferring QTL located on chromosome 7 between public marker isotig28625_2789 (SEQ ID NO: 59) and public marker isotig41937_218 (SEQ ID NO: 61) which represents an interval of 11.2 cM.

Furthermore, the previously detailed markers were also placed on the respective public maps. Because we did not have access to the segregating individuals for these maps to calculate an exact genetic distance, we placed them in intervals based on the public maps.

TABLE 6

Locus of reduced pyruvate QTLs as defined
by publicly available genetic markers

| Marker | Map | Chromosome | Approximate mapping position |
|---|---|---|---|
| SNP_11 | B9885 × B8667 | 2 | 87.4-90.2 |
| SNP_12 | B9885 × B8667 | 2 | 87.4-90.2 |
| SNP_13 | B9885 × B8667 | 2 | 92.4-93.4 |
| SNP_14 | B9885 × B8667 | 2 | 92.4-93.4 |
| SNP_01 | B9885 × B8667 | 2 | 98.3-112.8 |
| SNP_02 | B9885 × B8667 | 2 | 98.3-112.8 |
| SNP_03 | B9885 × B8667 | 2 | 98.3-112.8 |
| SNP_04 | B9885 × B8667 | 2 | 98.3-112.8 |
| SNP_15 | B9885 × B8667 | 2 | 116.1-127.4 |
| SNP_21 | Char × B5351 | 1 | 52.5-53.1 |

TABLE 6-continued

Locus of reduced pyruvate QTLs as defined
by publicly available genetic markers

| Marker | Map | Chromosome | Approximate mapping position |
|---|---|---|---|
| SNP_20 | Char × B5351 | 1 | 53.1-59.5 |
| SNP_19 | Char × B5351 | 1 | 53.1-59.5 |
| SNP_18 | Char × B5351 | 1 | 62.6-67.6 |
| SNP_05 | Char × B5351 | 1 | 67.6-70.1 |
| SNP_07 | Char × B5351 | 1 | 70.1-72.6 |
| SNP_06 | Char × B5351 | 1 | 70.1-72.6 |
| SNP_08 | Char × B5351 | 1 | 72.6-75.2 |
| SNP_17 | Char × B5351 | 1 | 72.6-85.9 |
| SNP_16 | Char × B5351 | 1 | 101.9-107.7 |
| SNP_10 | B9885 × B8667 | 7 | 0 |
| SNP_09 | B9885 × B8667 | 7 | 7.9-11.2 |
| SNP_25 | B9885 × B8667 | 7 | 7.9-11.2 |
| SNP_24 | B9885 × B8667 | 7 | 10.7-12.9 |
| SNP_23 | B9885 × B8667 | 7 | 17.3-18.4 |
| SNP_22 | B9885 × B8667 | 7 | 18.4 |

Example 2

Validation of QTL Markers

To validate that the identified markers are useful for predicting pyruvate level we genotyped a panel of lines with a range of pyruvate values. Five bulbs from each line were genotyped, and a pyruvate concentration was assigned based on the average for bulbs from that line.

Pyruvate measurements were made on bulbs after being stored for four months. A 5-10 mm thick slice was taken from the equator of an onion bulb (25-50 g). The slice was quartered, mixed with deionized water (1:10 dilution), and homogenized with an immersion blender until chunks disappeared (about 45 sec). One (1) mL of onion juice was centrifuged for 5 minutes (16,000×g at room temperature). Supernatant was used for pyruvate measurement, which was conducted according to Anthon and Barrett method (2003) with some modifications. Six (6) mL of onion juice was mixed with 50 mL of 0.025% dinitrophenylhydrazine (DNPH) reagent in a 96-well microplate. The mixture was incubated for 15 min at 37° C., and then mixed with 50 mL of 1.5N sodium hydroxide (NaOH). The mixture was cooled to room temperature before reading the absorbance at 515 nm. Pyruvate analysis was conducted in triplicate for each sample. A calibration curve was prepared using pyruvate standard solutions at 0.4, 0.8, and 1.2 mM. Results are reported in μmol of pyruvate per gram of fresh tissue (μmol/g).

The results of this validation confirmed that the reduced pungency haplotypes ("B" allele calls) were enriched in the reduced pungency lines, and the lines with lower average pyruvate values and less variation in pyruvate level had a lower occurrence of high pyruvate ("A") alleles (Table 7). For all reduced pungency material, the Soluble Solids Content (SSC) as measured by Brix was above 7% and was not correlated with pyruvate level ($R^2=0.2$ with a negative slope).

The linkage groups as described herein above were mapped to known markers to determine which chromosome number corresponds to each of the linkage groups. It was accordingly found that linkage group 3 corresponds to chromosome 2 of *Allium cepa*, linkage group 4 corresponds to chromosome 1 of *Allium cepa* and linkage group 6 corresponds to chromosome 7 of *Allium cepa*.

TABLE 7

Results of validation on reduced pungency plant material. Genotypes are coded in A/H/B format, where A is the high pungency allele, H is heterozygous, and B is the reduced pungency allele. The flanking SNP markers are underlined, whereas the peak markers are indicated in bold typeface (see also Table 2 as provided herein above). The corresponding base call for the reduced pungency allele is indicated in the row below the SNP marker names. Entries are ordered based on mean pyruvate levels first, and then standard deviation of pyruvate levels when the mean level is similar.

| Line name | Pyruvate mean (µmol/g) | Pyruvate min (µmol/g) | Pyruvate median (µmol/g) | Pyruvate max (µmol/g) | Pyruvate SD (µmol/g) | Brix mean | Number of bulbs | Chromosome 2 | | | | | |
|---|---|---|---|---|---|---|---|---|---|---|---|---|---|
| | | | | | | | | SNP_11 A | SNP_12 C | SNP_13 T | SNP_14 A | SNP_01 T | SNP_02 A |
| | | Base call for reduced pungency allele (B) | | | | | | | | | | | |
| Line 1 | 3.89 | 0.15 | 3.7 | 10.95 | 1.75 | 7.24 | 494 | H | H | B | B | A | H |
| | | | | | | | | B | B | B | B | A | B |
| | | | | | | | | H | H | B | B | A | B |
| | | | | | | | | H | H | B | B | A | H |
| | | | | | | | | B | B | B | B | A | H |
| Line 2 | 2.94 | 0.64 | 2.78 | 11.4 | 1.18 | 7.05 | 1213 | H | . | B | B | H | H |
| | | | | | | | | B | B | B | B | A | B |
| | | | | | | | | B | B | B | B | A | B |
| | | | | | | | | A | A | B | B | B | B |
| | | | | | | | | H | H | A | H | A | A |
| Line 3 | 2.88 | 0.88 | 2.73 | 6.67 | 1.18 | 7.88 | 185 | H | B | B | B | B | B |
| | | | | | | | | A | B | B | B | H | B |
| | | | | | | | | B | B | B | B | H | B |
| | | | | | | | | H | B | B | B | H | B |
| | | | | | | | | A | B | B | B | H | B |
| Line 4 | 1.97 | 0.33 | 1.84 | 9.7 | 0.82 | 7.83 | 950 | B | B | B | B | B | B |
| | | | | | | | | A | B | B | B | B | B |
| | | | | | | | | B | B | B | B | B | B |
| | | | | | | | | B | B | B | B | B | B |
| | | | | | | | | B | B | B | B | B | B |
| Line 5 | 2 | 0.69 | 1.9 | 4.4 | 0.65 | 7.95 | 148 | B | B | B | B | B | B |
| | | | | | | | | B | B | B | B | B | B |
| | | | | | | | | B | B | B | B | B | B |
| | | | | | | | | B | B | B | B | B | B |
| | | | | | | | | B | B | B | B | B | B |
| Line 6 | 1.48 | 0.35 | 1.3 | 4.35 | 0.69 | 7.4 | 405 | B | B | B | B | B | B |
| | | | | | | | | B | B | B | B | B | B |
| | | | | | | | | B | B | B | B | B | B |
| | | | | | | | | B | B | B | B | B | B |
| | | | | | | | | B | B | B | B | B | B |
| Line 7 | 1.47 | 0.46 | 1.38 | 6.24 | 0.57 | 7.69 | 489 | B | B | B | B | B | B |
| | | | | | | | | B | B | B | B | B | B |
| | | | | | | | | B | B | B | B | B | B |
| | | | | | | | | B | B | B | B | B | B |
| | | | | | | | | B | B | B | B | B | B |

| Line | Chromosome 2 | | | Chromosome 1 | | | | | | | | | |
|---|---|---|---|---|---|---|---|---|---|---|---|---|---|
| | SNP_03 C | SNP_04 T | SNP_15 G | SNP_16 A | SNP_17 A | SNP_08 T | SNP_06 A | SNP_07 C | SNP_05 C | SNP_18 T | SNP_19 T | SNP_20 G | SNP_21 C |
| Line 1 | B | B | B | A | A | A | B | A | A | B | A | A | B |
| | B | B | A | A | A | A | B | A | A | B | A | A | B |
| | B | H | A | A | A | A | B | A | A | B | A | A | B |
| | B | H | H | A | A | A | B | A | A | B | A | A | B |
| | B | H | B | A | A | A | B | A | A | B | A | A | B |
| Line 2 | H | H | B | A | H | H | H | B | H | B | H | B | H |
| | B | B | B | A | A | H | B | A | A | B | A | A | B |
| | B | B | B | A | A | H | B | A | A | B | A | A | B |
| | B | B | B | A | B | B | B | B | B | H | B | H | B |
| | A | A | B | A | B | B | B | B | B | B | A | B | H |
| Line 3 | B | B | B | B | B | B | B | B | B | B | B | B | B |
| | B | B | B | B | H | B | B | B | B | B | B | B | B |
| | B | B | B | B | B | B | B | B | B | B | B | B | B |
| | B | B | B | B | H | B | B | B | B | B | B | B | B |
| | B | B | B | B | B | B | B | B | B | B | B | B | B |
| Line 4 | B | B | B | B | H | B | B | B | B | B | B | B | B |
| | B | B | B | B | B | B | B | B | B | B | B | B | B |
| | B | B | B | B | H | B | B | B | B | B | B | B | B |
| | B | B | B | B | H | B | B | B | B | B | B | B | B |
| | B | B | B | B | B | B | . | B | B | B | B | B | B |

TABLE 7-continued

Results of validation on reduced pungency plant material. Genotypes are coded in A/H/B
format, where A is the high pungency allele, H is heterozygous, and B is the reduced pungency
allele. The flanking SNP markers are underlined, whereas the peak markers are indicated in bold
typeface (see also Table 2 as provided herein above). The corresponding base call for the re-
duced pungency allele is indicated in the row below the SNP marker names. Entries are ordered
based on mean pyruvate levels first, and then standard deviation of pyruvate levels when the
mean level is similar.

| | | | | | | | | | | | | | |
|---|---|---|---|---|---|---|---|---|---|---|---|---|---|
| Line | B | B | B | B | B | B | B | B | B | B | B | B | B |
| 5 | B | B | B | B | B | B | B | B | B | B | B | B | B |
| | B | B | B | B | B | B | B | B | B | B | B | B | B |
| | B | B | B | B | B | B | B | B | B | B | B | B | B |
| | B | B | B | B | B | B | B | B | B | B | B | B | B |
| Line | B | B | B | B | B | B | B | B | B | B | B | B | B |
| 6 | B | B | B | B | B | B | B | B | B | B | B | B | B |
| | B | B | B | B | B | B | B | B | B | B | B | B | B |
| | B | B | B | B | B | B | B | B | B | B | B | B | B |
| | B | B | B | B | B | B | B | B | B | B | B | B | B |
| Line | B | B | B | B | B | B | B | B | B | B | B | B | B |
| 7 | B | B | B | B | B | B | B | B | B | B | B | B | B |
| | B | B | B | B | B | B | B | B | B | B | B | B | B |
| | B | B | B | B | B | B | B | B | B | B | B | B | B |
| | B | B | B | B | B | B | B | B | B | B | B | B | B |

Chromosome 7

| | SNP_22 | SNP_23 | SNP_24 | SNP_25 | SNP_09 | SNP_10 |
|---|---|---|---|---|---|---|
| | T | T | C | G | T | G |
| Line | B | B | B | A | A | B |
| 1 | B | B | B | A | A | B |
| | B | B | B | A | A | B |
| | B | B | B | A | A | B |
| | B | B | B | A | A | B |
| Line | A | B | A | H | H | H |
| 2 | A | B | A | A | A | B |
| | A | B | A | A | A | B |
| | A | B | A | B | B | A |
| | A | B | A | B | B | H |
| Line | A | B | B | B | B | H |
| 3 | A | B | B | B | B | B |
| | B | B | B | B | B | H |
| | H | B | B | B | B | B |
| | H | B | B | B | B | B |
| Line | B | B | B | B | B | H |
| 4 | H | B | B | B | B | B |
| | H | B | B | B | B | H |
| | H | B | B | B | B | H |
| | B | B | B | B | B | B |
| Line | B | B | B | B | B | B |
| 5 | B | B | B | B | B | B |
| | B | B | B | B | B | B |
| | B | B | B | B | B | B |
| | B | B | B | B | B | B |
| Line | B | B | B | B | B | B |
| 6 | H | B | B | B | B | B |
| | B | B | B | B | B | B |
| | B | B | B | B | B | B |
| | B | B | B | B | B | B |
| Line | B | B | B | B | B | B |
| 7 | B | B | B | B | B | B |
| | B | B | B | B | B | B |
| | B | B | B | B | B | B |
| | B | B | B | B | B | B |

79

The invention claimed is:

1. A method for producing an *Allium cepa* plant or plant part comprising a Quantitative Trait Loci (QTL) conferring a reduced pyruvate level when compared to an *Allium cepa* plant or plant part not comprising said QTL, said method comprising:

crossing an *Allium cepa* plant comprising said QTL conferring a reduced pyruvate level with another *Allium cepa* plant, and selecting for offspring from the crossing comprising one or more markers linked to a reduced pyruvate conferring QTL located on chromosome 1 flanked by the markers SNP_17 comprising an Adenine at nucleotide 51 of SEQ ID NO: 33 and SNP_18 comprising a Thymine at nucleotide 51 of SEQ ID NO: 35 by selecting said one or more markers based on marker assisted selection;

wherein said QTL conferring a reduced pyruvate level is as present in a plant of which seeds were deposited under Accession No. PTA-9053, a plant of which seeds were deposited under Accession No. PTA-9054 or a plant of which seeds were deposited under Accession No. PTA-9055.

2. The method according to claim 1, wherein the marker is a fragment length polymorphism (RFLP) marker, a cleaved amplified polymorphic sequence (CPAS) marker, a microsatellite marker, a restriction fragment length polymorphism (RFLP) marker, a random amplification of polymorphic DNA (RAPD) marker, an amplified fragment length polymorphism (AFLP) marker, or a single nucleotide polymorphism (SNP) marker.

3. The method according to claim 2, wherein the marker linked to a reduced pyruvate conferring QTL located on chromosome 1 is a SNP marker of: SNP_17 comprising an Adenine at nucleotide 51 of SEQ ID NO: 33; SNP_05 comprising a Cytosine at nucleotide 51 of SEQ ID NO: 9; SNP_06 comprising an Adenine at nucleotide 51 of SEQ ID NO: 11; SNP_07 comprising a Cytosine at nucleotide 51 of SEQ ID NO: 13; SNP_08 comprising a Thymine at nucleotide 51 of SEQ ID NO: 15; and/or SNP_18 comprising a Thymine at nucleotide 51 of SEQ ID NO: 35.

4. The method according to claim 2, wherein the marker on chromosome 1 is SNP_07 comprising a Cytosine at nucleotide 51 of SEQ ID NO: 13.

5. A genotyping array comprising two or more SNPs of:
SNP_01 comprising a Thymine at nucleotide 51 of SEQ ID NO: 1;
SNP_02 comprising an Adenine at nucleotide 51 of SEQ ID NO: 3;
SNP_03 comprising a Cytosine at nucleotide 51 of SEQ ID NO: 5;
SNP_04 comprising a Thymine at nucleotide 51 of SEQ ID NO: 7;
SNP_05 comprising a Cytosine at nucleotide 51 of SEQ ID NO: 9;
SNP_06 comprising an Adenine at nucleotide 51 of SEQ ID NO: 11;
SNP_07 comprising a Cytosine at nucleotide 51 of SEQ ID NO: 13;
SNP_08 comprising a Thymine at nucleotide 51 of SEQ ID NO: 15;
SNP_09 comprising a Thymine at nucleotide 51 of SEQ ID NO: 17;

SNP_10 comprising a Guanine at nucleotide 51 of SEQ ID NO: 19;
SNP_11 comprising an Adenine at nucleotide 51 of SEQ ID NO: 21;
SNP_12 comprising a Cytosine at nucleotide 51 of SEQ ID NO: 23;
SNP_13 comprising a Thymine at nucleotide 51 of SEQ ID NO: 25;
SNP_14 comprising an Adenine at nucleotide 51 of SEQ ID NO: 27;
SNP_15 comprising a Guanine at nucleotide 51 of SEQ ID NO: 29;
SNP_16 comprising an Adenine at nucleotide 51 of SEQ ID NO: 31;
SNP_17 comprising an Adenine at nucleotide 51 of SEQ ID NO: 33;
SNP_18 comprising a Thymine at nucleotide 51 of SEQ ID NO: 35;
SNP_19 comprising a Thymine at nucleotide 51 of SEQ ID NO: 37;
SNP_20 comprising a Guanine at nucleotide 51 of SEQ ID NO: 39;
SNP_21 comprising a Cytosine at nucleotide 51 of SEQ ID NO: 41;
SNP_22 comprising a Thymine at nucleotide 51 of SEQ ID NO: 43;
SNP_23 comprising a Thymine at nucleotide 51 of SEQ ID NO: 45;
SNP_24 comprising a Cytosine at nucleotide 51 of SEQ ID NO: 47; and/or
SNP_25 comprising a Guanine at nucleotide 51 of SEQ ID NO: 49.

6. A method for producing an *Allium cepa* plant or plant part comprising a Quantitative Trait Loci (QTL) conferring a reduced pyruvate level when compared to an *Allium cepa* plant or plant part not comprising said QTL, said method comprising:

crossing an *Allium cepa* plant comprising said QTL conferring a reduced pyruvate level with another *Allium cepa* plant, and selecting for offspring from the crossing comprising one or more markers linked to a reduced pyruvate conferring QTL located on chromosome 1 flanked by the markers SNP_05 comprising a Cytosine at nucleotide 51 of SEQ ID NO: 9 and SNP_08 comprising a Thymine at nucleotide 51 of SEQ ID NO: 15 by selecting said one or more markers based on marker assisted selection;

wherein said QTL conferring a reduced pyruvate level is as present in a plant of which seeds were deposited under Accession No. PTA-9053, a plant of which seeds were deposited under Accession No. PTA-9054 or a plant of which seeds were deposited under Accession No. PTA-9055.

7. The method according to claim 3, wherein the marker linked to a reduced pyruvate conferring QTL located on chromosome 1 is a SNP marker of: SNP_05 comprising a Cytosine at nucleotide 51 of SEQ ID NO: 9; SNP_06 comprising an Adenine at nucleotide 51 of SEQ ID NO: 11; SNP_07 comprising a Cytosine at nucleotide 51 of SEQ ID NO: 13; and/or SNP_08 comprising a Thymine at nucleotide 51 of SEQ ID NO: 15.

* * * * *